United States Patent [19]
Langlois et al.

[11] Patent Number: 5,849,781
[45] Date of Patent: Dec. 15, 1998

[54] TRICYCLIC AMIDES

[75] Inventors: Michel Langlois, Sceaux; Monique Mathe-Allainmat, Massy; Philippe Delagrange, Issy-les-Moulineaux; Pierre Renard, Versailles; Béatrice Guardiola, Saint-Cloud, all of France

[73] Assignee: Adir Et Compagnie, Courbevoie, France

[21] Appl. No.: 942,177

[22] Filed: Oct. 1, 1997

Related U.S. Application Data

[62] Division of Ser. No. 631,196, Apr. 12, 1996, Pat. No. 5,712,312.

[30] Foreign Application Priority Data

Apr. 14, 1995 [FR] France .................................. 9504503

[51] Int. Cl.$^6$ .......................... A61K 31/34; A61K 31/40; C07D 209/56; C07D 307/77
[52] U.S. Cl. .......................... 514/411; 514/337; 514/339; 514/443; 514/468; 546/276.7; 546/281.1; 546/284.1; 548/436; 548/437; 548/438; 549/43; 549/44; 549/45; 549/47; 549/458
[58] Field of Search .................................. 548/436, 437, 548/438; 549/43, 44, 45, 47, 458; 514/411, 443, 468

[56] References Cited

U.S. PATENT DOCUMENTS

| 5,244,911 | 9/1993 | Booher et al. ........................... 514/339 |
| 5,244,912 | 9/1993 | Booher et al. ........................... 514/339 |
| 5,470,853 | 11/1995 | Flaugh et al. ......................... 514/232.8 |

FOREIGN PATENT DOCUMENTS

| 0041293 | 12/1981 | European Pat. Off. . |
| 0153083 | 8/1985 | European Pat. Off. . |
| 0162695 | 11/1985 | European Pat. Off. . |

OTHER PUBLICATIONS

Pickering, et al. British Journal of Pharmacology 119, No. 2, pp. 379–387, Sep. 1996; "Analogs of diverse structure are unable to differentiate native melatonin receptors in the chicken retina, sheep parts tuuberalis and Xenopus melanophores".
Haefliger et al., Chemical Abstracts, vol. 98, abstract 126427, 1983.
Pickering et al., Chemical Abstracts, vol. 125, abstact 293301, 1996.
Spadoni et al., Chemical Abstracts, vol. 127, abstract 34048, 1997.
C. Evans et al., Reactions of 2,3–Dihydro–4–methylphenalen–1 one J. Chem. Soc. (C), 1971 pp. 1607–1609.
Wieringa et al., Chemical Abstracts, vol. 96, abstract 122465h (1982).
Heindl et al. Chemical Abstracts, vol. 106, abstract 1562272h (1987).

*Primary Examiner*—Richard L. Raymond
*Attorney, Agent, or Firm*—Gordon W. Hueschen

[57] ABSTRACT

The invention relates to a compound selected from these of formula (I):

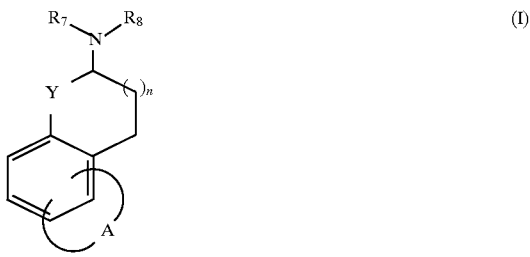

in which $R_7$, $R_8$, Y, n and A are as defined in the description, and medicinal product containing the same useful for treating a disorder of the melatoninergic system.

17 Claims, No Drawings

TRICYCLIC AMIDES

The present application is a division of our prior-filed application Ser. No. 08/631,196, filed Apr. 12, 1996, now U.S. Pat. No. 5,712,312 issued Jan. 27, 1998.

The invention relates to novel tricyclic amides, to processes for their preparation and to the pharmaceutical compositions which contain them.

The invention describes novel tricyclic amides which prove to be powerful melatoninergic receptor ligands.

N-(4-Methyl-2,3-dihydro-1H-phenalen-2-yl)acetamide is already described in the literature (Waite D. et al., J. Chem. Soc. 1971, (9), pp. 1607–1609) but no pharmacological activity is taught with regard to this compound.

Certain tricyclic amide derivatives of benzo[cd]indole type are known (EP 153,083 and EP 162,695) but only as intermediates in the synthesis of amine derivatives intended for serotoninergic purposes.

In the last ten years, many studies have demonstrated the fundamental role of melatonin (5-methoxy-N-acetyltryptamine) in controlling the circadian rhythm and endocrine functions, and melatonin receptors have been characterized and located.

Besides their beneficial action on circadian rhythm disorders (J. Neurosurg. 1985, 63, pp. 321–341) and on sleeping disorders (Psychopharmacology, 1990, 100, pp. 222–226), ligands for the melatoninergic system possess advantageous pharmacological properties on the central nervous system, in particular anxiolytic and antipsychotic properties (Neuropharmacology of Pineal Secretions, 1990, 8 (3–4), pp. 264–272) and analgesic properties (Pharmacopsychiat., 1987, 20, pp. 222–223) as well as for the treatment of Parkinson's disease (J. Neurosurg. 1985, 63, pp. 321–341) and Alzheimer's disease (Brain Research, 1990, 528, pp. 170–174). Similarly, these compounds have shown activity on certain cancers (Melatonin—Clinical Perspectives, Oxford University Press, 1988, page 164–165), on ovulation (Science 1987, 227, pp. 714–720) and on diabetes (Clinical Endocrinology, 1986, 24, pp. 359–364).

Compounds which make it possible to act on the melatoninergic system are thus excellent medical products for the clinician for the treatment of pathologies associated with the melatoninergic system and especially those mentioned above.

The invention relates to the compounds of formula (I):

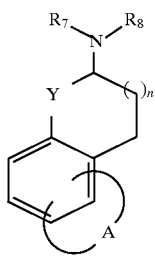

in which A forms, with the group to which it is attached, a tricyclic group chosen from $(A_1)$ to $(A_4)$:

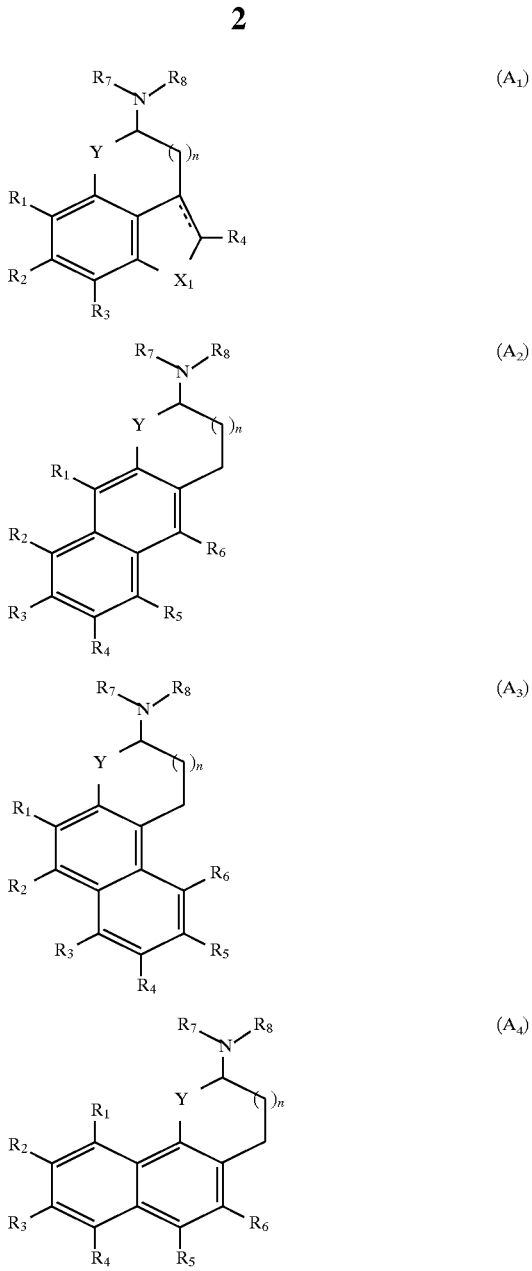

in which:
$R_1$, $R_2$, $R_3$, $R_4$, $R_5$ and $R_6$ represent, independently of each other, a hydrogen or a radical chosen from halogen, hydroxyl, Ra and —O—Ra; with Ra representing a radical chosen from alkyl, alkyl sybstituted with one or more halogens, alkenyl, alkynyl, cycloalkyl, cycloalkylalkyl, aryl, substituted aryl, arylalkyl and substituted arylalkyl;

$X_1$ represents a group chosen from sulfur, oxygen, —C($R_5$)=C($R_6$)—, —C($R_5$)($R_5$')—C($R_6$)($R_6$')—, —C($R_5$)($R_5$')—C($R_6$)=, —C($R_5$)($R_5$')— and —N($R_{14}$)— where $R_5$ and $R_6$ are as defined above and $R_5$' and $R_6$' are chosen from the same meanings as those of $R_1$, $R_2$, $R_3$, $R_4$, $R_5$ and $R_6$, as defined above, and $R_{14}$ represents a hydrogen or a radical chosen from alkyl, aryl, arylalkyl, substituted aryl and substituted arylalkyl, the bond - - - - means that this bond may be a single or double bond, Y represents a group —C(R$_9$)(R$_{10}$)— in which R$_9$ and R$_{10}$ represent, independently of each other, a hydrogen, an alkyl or an alkoxy, n represents an integer from 1 to 3;

R$_7$ represents a hydrogen or a radical R$_7$' chosen from alkyl, aryl, arylalkyl, substituted aryl and substituted arylalkyl and R$_8$ represents:

a group of formula —CO—R$_{11}$ in which R$_{11}$ represents a radical R$_{12}$ with R$_{12}$ representing a hydrogen or a radical chosen from alkyl, alkyl substituted with one or more halogens, alkenyl, alkynyl, cycloalkyl, cycloalkylalkyl, aryl, substituted aryl, arylalkyl or substituted arylalkyl, or R$_{11}$ represents a radical —NH—R$_{13}$, with R$_{13}$ representing a hydrogen atom or a radical chosen from alkyl, alkyl substituted with one or more halogens, alkenyl, alkynyl, cycloalkyl, cycloalkylalkyl, aryl, substituted aryl, arylalkyl and substituted arylalkyl;

or a group of formula —CS—R$_{11}$ in which R$_{11}$ is as defined above with the proviso that the compound of formula (I) cannot represent N-(4-methyl-1H-2,3-dihydro-phenalen-2-yl) acetamide, and that, is X, represents —NH— or —N(CH$_3$)— then R$_1$ cannot be hydrogen or halogen, the enantiomers and diastereoisomers thereof and the addition salts thereof with a pharmaceutically acceptable base, it being understood that:

the terms "alkyl" and "alkoxy" denote linear or branched radicals of 1 to 6 carbon atoms, the terms "alkenyl" and "alkynyl" represent unsaturated linear or branched radicals of 2 to 6 carbon atoms, the term "cycloalkyl" denotes a cyclic group of 3 to 8 carbon atoms, the term "aryl" denotes a naphthyl, a phenyl or a pyridyl, the expression "substituted" associated with the terms "aryl" and "arylalkyl" means that these groups are substituted with one or more radicals chosen from halogen, alkyl, alkyl substituted with one or more halogens, alkoxy and hydroxyl.

The invention relates particularly to the compounds of formula (I) in which, taken separately or together as appropriate, A represents a group A$_1$, A represents a group A$_2$, A represents a group A$_3$, A represents a group A$_4$, X$_1$ represents a sulfur, X$_1$ represents an oxygen, X$_1$ represents a group —N(R$_{14}$)—, X$_1$ represents a group —C(R$_5$)=C(R$_6$)—

X$_1$ represents a group —C(R$_5$)(R$_5$')—C(R$_6$)(R$_6$')— where appropriate, R$_1$, R$_2$, R$_3$, R$_4$, and R$_5$, R$_5$', R$_6$ and R$_6$' simultaneously represent hydrogens, where appropriate, one of the radicals R$_1$, R$_2$, R$_3$, R$_4$, and R$_5$, R$_5$', R$_6$ and R$_6$' is a radical chosen from halogen, alkyl and alkoxy, for example alkoxy, and the others represent hydrogens, Y represents a methylene group, n is equal to 1, R$_7$ represents a hydrogen, R$_7$ represents an alkyl, R$_8$ represents a group —CO—R$_{11}$, R$_8$ represents a group —CS—R$_{11}$, R$_{11}$ represents an alkyl, R$_{11}$ represents a cycloalkyl, R$_{11}$ represents a group —NH—R$_{13}$, R$_{13}$ represents an alkyl, and R$_{13}$ represents a cycloalkyl.

For example, the invention relates to the specific compounds of formula (I) corresponding to the formulae (1) to (21):

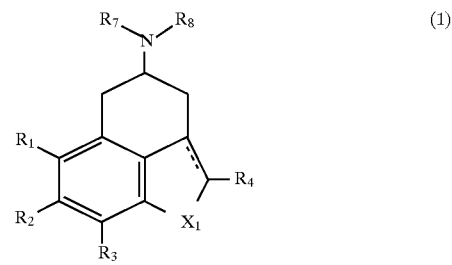

(1)

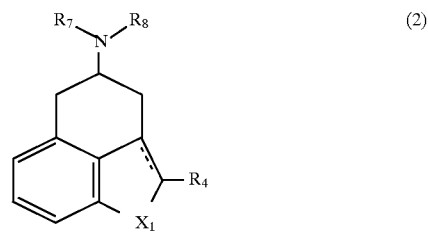

(2)

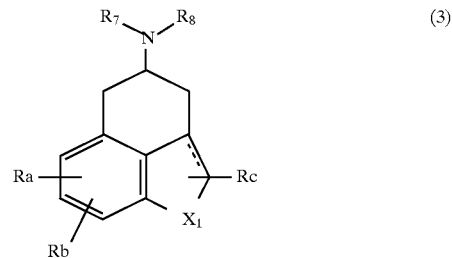

(3)

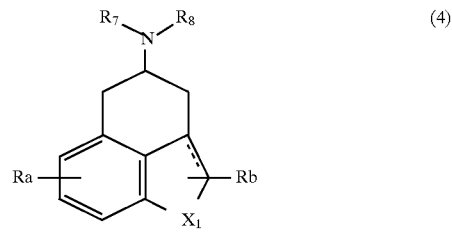

(4)

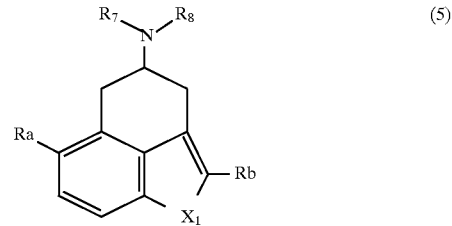

(5)

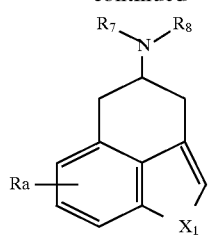
(6)
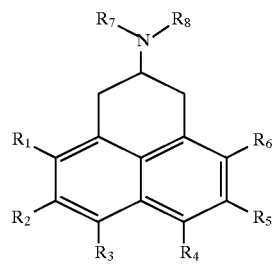
(7)
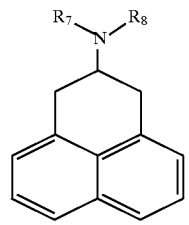
(8)
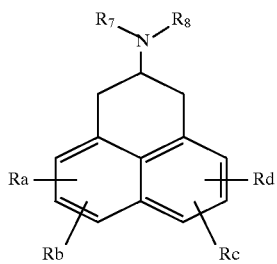
(9)
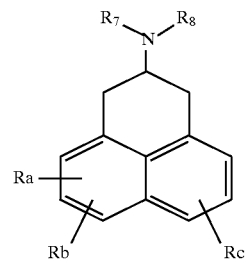
(10)
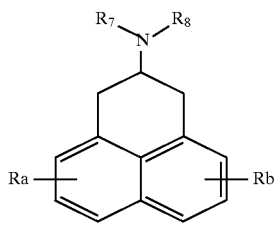
(11)
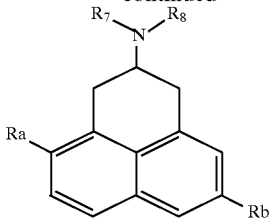
(12)
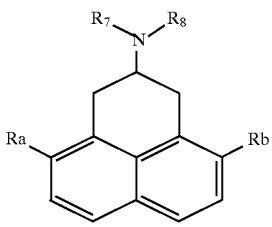
(13)
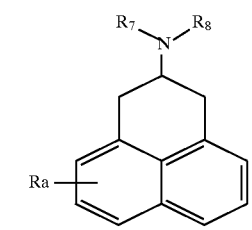
(14)
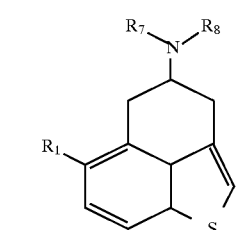
(15)
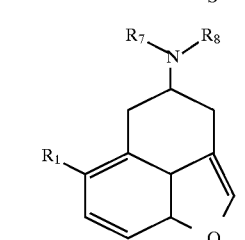
(16)
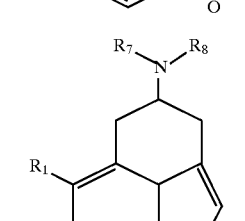
(17)
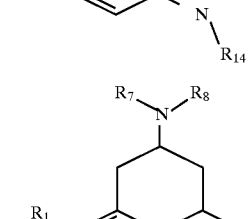
(18)

-continued

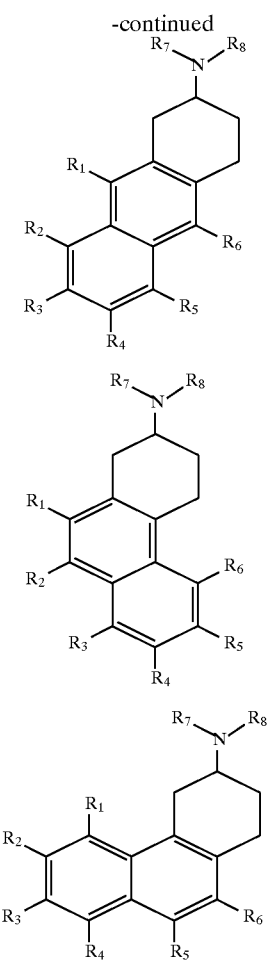

in which $X_1$, $R_1$, $R_2$, $R_3$, $R_4$, $R_5$, $R_6$, $R_7$ and $R_8$ are as defined in formula (I) and Ra, Rb, Rc and Rd may be chosen from the same values as those defined for $R_1$, $R_2$, $R_3$, $R_4$, $R_5$, and $R_6$ with the exception of hydrogen.

For example Ra, Rb, Rc and Rd are chosen from halogen, alkyl and alkoxy.

For example, $X_1$ represents a group chosen from sulfur, oxygen, —C($R_5$)=C($R_6$)—, —C($R_5'$)($R_5$)—C($R_6$)($R_6'$)—, —C($R_5$)($R_5'$)—C($R_6$)= and —C($R_5$)($R_5'$)—. in which $R_5$, $R_5'$, $R_6$ and $R_6'$ are as defined above.

Specifically, the alkyl radicals present in the formula (I) may be chosen from methyl, ethyl, n-propyl, isopropyl, n-butyl, isobutyl, sec-butyl, tert-butyl, pentyl and hexyl, as well as the skeleton isomers of the pentyl and hexyl radicals.

The alkoxy radicals present in the formula (I) may be chosen from methoxy, ethoxy, n-propoxy, isopropoxy, n-butoxy, iso-butoxy, sec-butoxy, tert-butoxy, pentyloxy and hexyloxy.

The halogens present in the formula (I) may be chosen from bromine, chlorine, fluorine and iodine.

The cycloalkyls present in the formula (I) may be chosen from cyclopropyl, cyclobutyl, cyclopentyl, cyclohexyl, cycloheptyl and cyclooctyl.

The alkenyls present in the formula (I) may be chosen from vinyl, allyl, propenyl, butenyl, pentenyl and hexenyl? and the alkynyls present in the formula (I) may be chosen from ethynyl, propynyl, 2-propynyl, butynyl, pentynyl and hexynyl, as well as the different isomers of these radicals according to the position of the double or triple bond.

Among the pharmaceutically acceptable bases which may be used to form an addition salt with the compounds of the invention, non-limiting examples which may be mentioned are sodium hydroxide, potassium hydroxide, calcium hydroxide and aluminum hydroxide, alkali metal carbonates or alkaline-earth metal carbonates and organic bases such as triethylamine, benzylamine, diethanolamine, tert-butylamine, dicyclohexylamine and arginine.

The invention also relates to the process for the preparation of compounds of formula ($A_1$) as defined in formula (I), in which process a compound of formula (II):

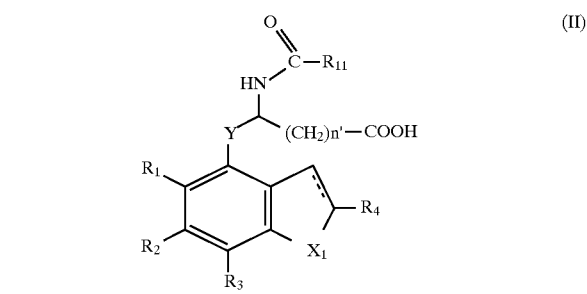

in which $R_1$, $R_2$, $R_3$, $R_4$, $R_{11}$, $X_1$ and Y are as defined in formula (I), and n' represents 0, 1 or 2, is cyclized to give a compound of formula (III):

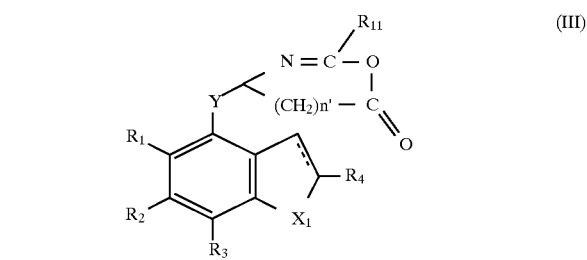

in which $R_1$, $R_2$, $R_3$, $R_4$, $R_{11}$, n', $X_1$ and Y are as defined above, which compound is then reacted with a Lewis acid to give a compound of formula (IV):

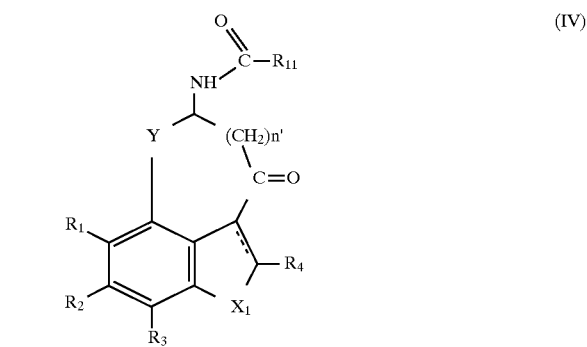

in which $R_1$, $R_2$, $R_3$, $R_4$, $R_{11}$, n', $X_1$ and Y are as defined above, which compound is then reduced to give the compound of formula (I/a):

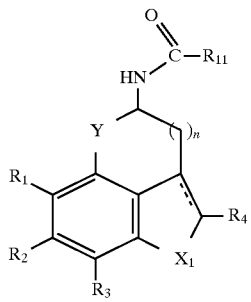
(I/a)

in which $R_1$, $R_2$, $R_3$, $R_4$, $R_{11}$, n, $X_1$ and Y are as defined above and n is as defined in formula (I), which compound of formula (I/a) is subjected to a thionating agent, such as Lawesson's reagent, to give the compound of formula (I/b):

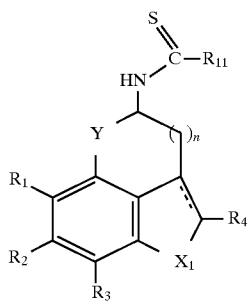
(I/b)

in which $R_1$, $R_2$, $R_3$, $R_4$, $R_{11}$, n, $X_1$ and Y are as defined above, it being possible for the compound of formula (I/a) or (I/b) to be reacted with a compound of formula (V):

  (V)

in which $R_7'$ is as defined in formula (I) and Hal represents a halogen atom, to give the corresponding compound of formula (I/c):

(I/c)

in which $R_1$, $R_2$, $R_3$, $R_4$, $R_{11}$, $R_7'$, n, $X_1$ and Y are as defined above, and X represents an oxygen or a sulfur, it being possible for the compounds of formula (I) to be:

purified according to one or more purification methods chosen from crystallization, chromatography, extraction, filtration and passage over charcoal or resin, separated, in pure form or in the form of a mixture, into the possible enantiomers or diastereoisomers thereof, and salified with a pharmaceutically acceptable base.

The invention thus relates to the process for the preparation of the compounds of formula (I-1):

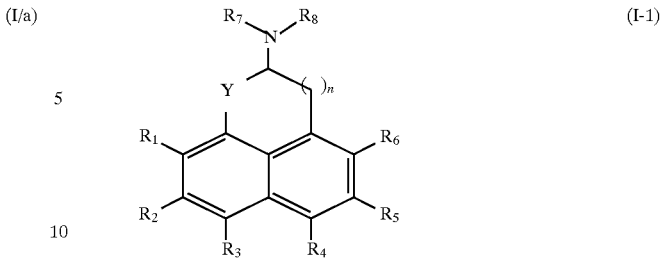
(I-1)

in which $R_1$, $R_2$, $R_3$, $R_4$, $R_5$, $R_6$, $R_7$, $R_8$, n and Y are as defined in formula (I) in which process a compound of formula (II-1):

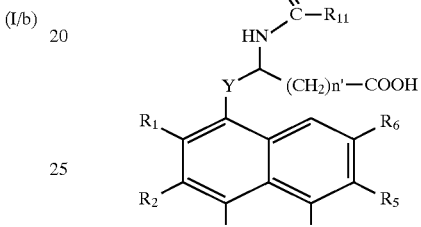
(II-1)

in which $R_1$, $R_2$, $R_3$, $R_4$, $R_5$, $R_6$, $R_{11}$ and Y are as defined in formula (I), and n' represents 0, 1 or 2, is cyclized to give a compound of formula (III-1):

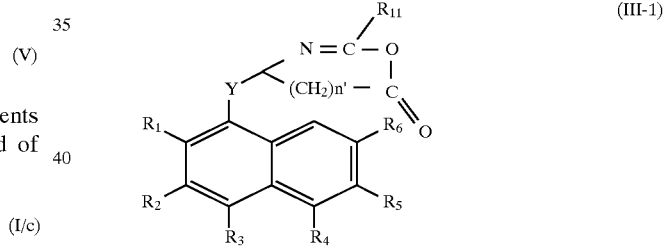
(III-1)

in which $R_1$, $R_2$, $R_3$, $R_4$, $R_5$, $R_6$, $R_{11}$, n' and Y are as defined above, which compound is then reacted with a Lewis acid to give a compound of formula (IV-1):

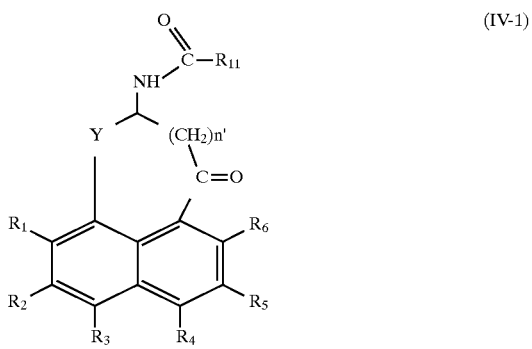
(IV-1)

in which $R_1$, $R_2$, $R_3$, $R_4$, $R_5$, $R_6$, $R_{11}$, n' and Y are as defined above, which compound is then reduced to give the compound of formula (I/a-1):

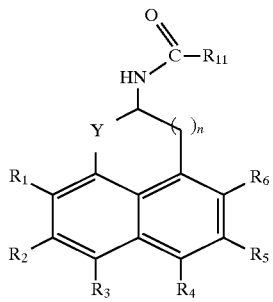

in which $R_1, R_2, R_3, R_4, R_5, R_6, R_{11}$, n and Y are as defined above and n is as defined in formula (I), which compound of formula (I/a-1) is subjected to a thionating agent, such as Lawesson's reagent, to give the compound of formula (I/b-1):

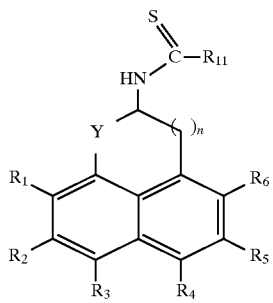

in which $R_1, R_2, R_3, R_4, R_5, R_6, R_{11}$, n and Y are as defined above, it being possible for the compound of formula (I/a) or (I/b) to be reacted with a compound of formula (V):

  (V)

in which $R_7'$ is as defined in the formula (I) and Hal represents a halogen atom, to give the corresponding compound of formula (I/c-1):

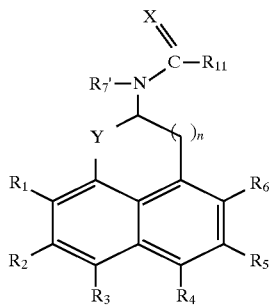

in which $R_1, R_2, R_3, R_4, R_5, R_6, R_{11}, R_7'$, n and Y are as defined above, and X represents an oxygen or a sulfur, the compounds of formulae (I/a-1), (I/b-1) and (I/c-1) together forming the compounds of formula (I-1), it being possible for the compounds of formula (I-1) to be:

purified according to one or more purification methods chosen from crystallization, chromatography, extraction, filtration and passage over charcoal or resin, separated, in pure form or in the form of a mixture, into the possible enantiomers or diastereoisomers thereof, and salified with a pharmaceutically acceptable base.

For example, the invention relates to the process for the preparation of the compounds of formula (I/d):

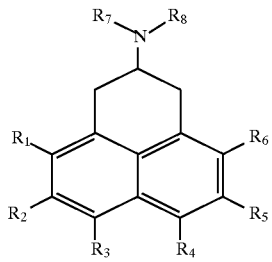

in which $R_1, R_2, R_3, R_4, R_5, R_6, R_7$ and $R_8$ are as defined in formula (I), in which process a compound of formula (II/d):

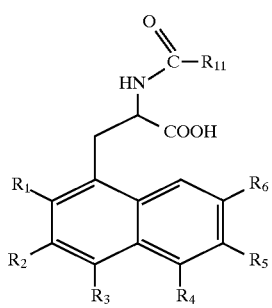

in which $R_1, R_2, R_3, R_4, R_5$ and $R_6$ are as defined above and $R_{11}$ is as defined in formula (I), is cyclized to give a compound of formula (III/d):

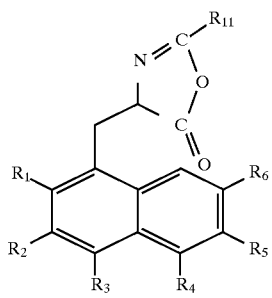

in which $R_1, R_2, R_3, R_4, R_5, R_6$ and $R_{11}$ are as defined above, which compound is then reacted with a Lewis acid to give a compound of formula (IV/d):

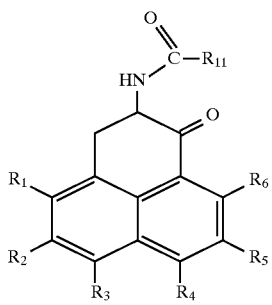

in which $R_1, R_2, R_3, R_4, R_5, R_6$ and $R_{11}$ are as defined above, which compound is then reduced to give the compound of formula (I/d1):

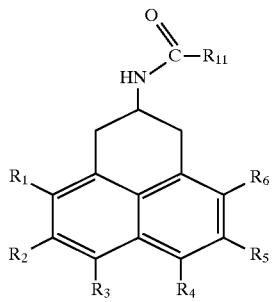

in which $R_1$, $R_2$, $R_3$, $R_4$, $R_5$, $R_6$ and $R_{11}$ are as defined above, which compound of formula (I/d1) is subjected to a thionating reagent, such as Lawesson's reagent, to give a compound of formula (I/d2):

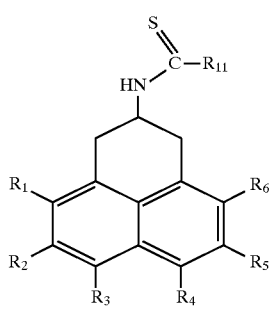

in which $R_1$, $R_2$, $R_3$, $R_4$, $R_5$, $R_6$ and $R_{11}$ are as defined above, it being possible for the compounds of formulae (I/d1) and (I/d2) to be reacted with a compound of formula (V):

in which $R_7'$ is as defined in formula (I) and Hal represents a halogen atom, to give a compound of formula (I/d3):

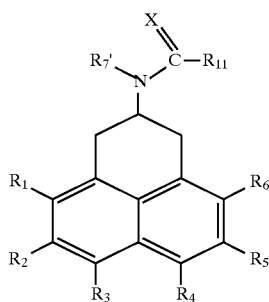

in which $R_1$, $R_2$, $R_3$, $R_4$, $R_5$, $R_6$, $R_{11}$ and $R_7'$ are as defined above and X represents an oxygen or a sulfur, the compounds of formulae (I/d1), (I/d2) and (I/d3) together forming the compounds of formula (I/d), it being possible for the compounds of formula (I/d) to be:

- purified according to one or more purification methods chosen from crystallization, chromatography, extraction, filtration and passage over charcoal or resin,
- separated, in pure form or in the form of a mixture, into the possible enantiomers or diastereoisomers thereof,
- and salified with a pharmaceutically acceptable base.

The invention also relates to the process for the preparation of the compounds of formula (I), in which process a compound of formula (g-VI):

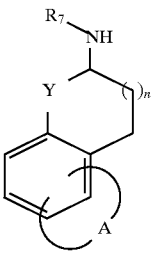

in which A, $R_7$, n and Y are as defined in formula (I), is reacted either with a compound of formula (VII) or (VIIa):

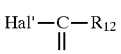

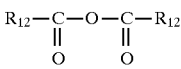

in which $R_{12}$ is as defined in formula (I), the anhydride of formula (VIIa) being mixed or symmetrical, and Hal' represents a halogen, to give a compound of formula (g-I/e):

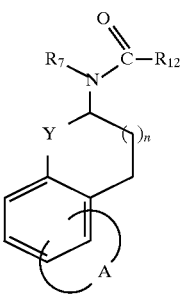

in which A, $R_7$, $R_{12}$, n and Y are as defined above, which compound is then subjected to a thionating reagent, such as Lawesson's reagent to give a compound of formula (g-I/e'):

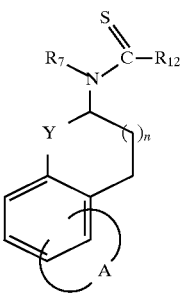

in which A, $R_7$, $R_{12}$, Y and n are as defined above, or with a compound of formula (VIII):

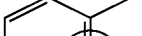

in which $R_{13}$ is as defined in formula (I) and X represents an oxygen or a sulfur, to give a compound of formula (g-I/f):

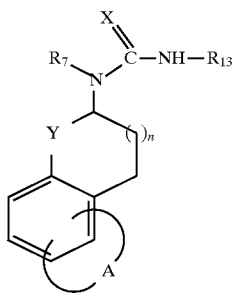 (g-I/f)

in which A, R$_7$, R$_{13}$, n, X and Y are as defined above, the compounds of formulae (g-I/e), (g-I/e') and (g-I/f) together forming the compounds of formula (I), it being possible for the compounds of formula (I) thus obtained to be:

- purified according to one or more purification methods chosen from crystallization, chromatography, extraction, filtration and passage over charcoal or resin,
- separated, in pure form or in the form of a mixture, into the possible enantiomers or diastereoisomers thereof,
- and salified with a pharmaceutically acceptable base.

The invention relates in particular to the process for the preparation of the compounds of formula (A/1), in which process a compound of formula (VI):

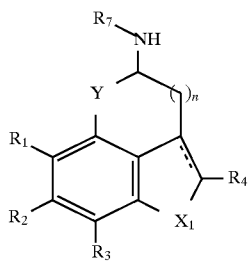 (VI)

in which R$_1$, R$_2$, R$_3$, R$_4$, R$_7$, n, X$_1$ and Y are as defined in formula (I), is reacted either with a compound of formula (VII) or (VIIa):

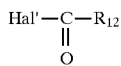 (VII)

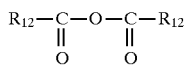 (VIIa)

in which R$_{12}$ is as defined in formula (I), the anhydride of formula (VIIa) being mixed or symmetrical, and Hal' represents a halogen, to give a compound of formula (I/e):

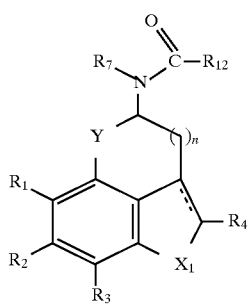 (I/e)

in which R$_1$, R$_2$, R$_3$, R$_4$, R$_7$, R$_{12}$, n, X$_1$ and Y are as defined above, which compound is then subjected to a thionating reagent, such as Lawesson's reagent, to give a compound of formula (I/e'):

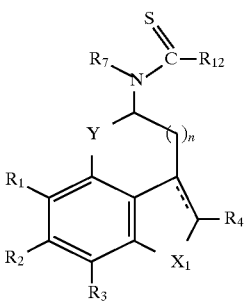 (I/e')

in which R$_1$, R$_2$, R$_3$, R$_4$, R$_7$, R$_{12}$, X$_1$, Y and n are as defined above, or with a compound of formula (VIII):

$$X\!=\!C\!=\!N\!-\!R_{13}$$ (VIII)

in which R$_{13}$ is as defined in formula (I) and X represents an oxygen or a sulfur, to give a compound of formula (I/f):

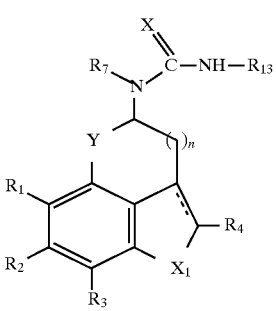 (I/f)

in which R$_1$, R$_2$, R$_3$, R$_4$, R$_7$, R$_{13}$, n, X$_1$, X and Y are as defined above, it being possible for the compounds of formula (I) thus obtained to be:

- purified according to one or more purification methods chosen from crystallization, chromatography, extraction, filtration and passage over charcoal or resin,
- separated, in pure form or in the form of a mixture, into the possible enantiomers or diastereoisomers thereof,
- and salified with a pharmaceutically acceptable base.

The invention thus relates to the process for the preparation of the compounds of formula (I-1) as defined above, in which process a compound of formula (VI-1):

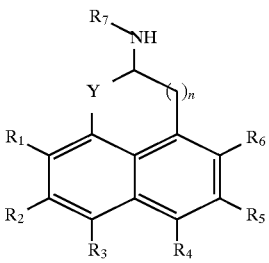 (VI-1)

in which R$_1$, R$_2$, R$_3$, R$_4$, R$_5$, R$_6$, R$_7$, n and Y are as defined in formula (I), is reacted either with a compound of formula (VII) or (VIIa):

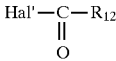 (VII)

-continued

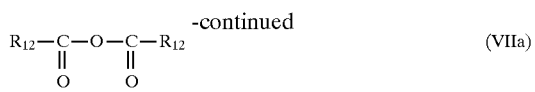 (VIIa)

in which $R_{12}$ is as defined in formula (I), the anhydride of formula (VIIa) being mixed or symmetrical, and Hal' represents a halogen, to give a compound of formula (I/e-1):

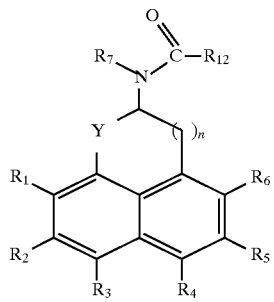 (I/e-1)

in which $R_1$, $R_2$, $R_3$, $R_4$, $R_5$, $R_6$, $R_7$, $R_{12}$, n and Y are as defined above, which compound is then subjected to a thionating reagent, such as Lawesson's reagent, to give a compound of formula (I/e'-1):

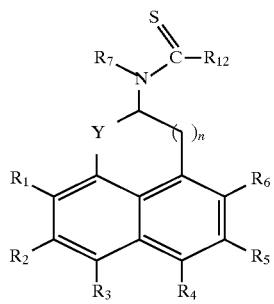 (I/e'-1)

in which $R_1$, $R_2$, $R_3$, $R_4$, $R_5$, $R_6$, $R_7$, $R_{12}$, Y and n are as defined above, or with a compound of formula (VIII):

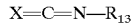 (VIII)

in which $R_{13}$ is as defined in formula (I) and X represents an oxygen or a sulfur, to give a compound of formula (I/f-1):

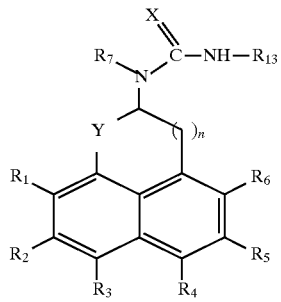 (I/f-1)

in which $R_1$, $R_2$, $R_3$, $R_4$, $R_5$, $R_6$, $R_7$, $R_{13}$, n, X and Y are as defined above, the compounds of formulae (I/e-1), (I/e'-1) and (I/f-1) together forming compounds of formula (I-1), it being possible for the compounds of formula (I-1) thus obtained to be:

purified according to one or more purification methods chosen from crystallization, chromatography, extraction, filtration and passage over charcoal or resin, separated, in pure form or in the form of a mixture, into the possible enantiomers or diastereoisomers thereof, and salified with a pharmaceutically acceptable base.

For example, the invention relates to the process for the preparation of compounds of formula (I/d):

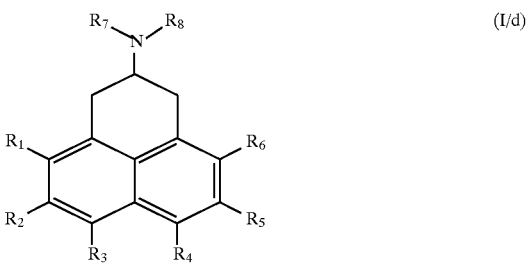 (I/d)

in which $R_1$, $R_2$, $R_3$, $R_4$, $R_5$, $R_6$, $R_7$ and $R_8$ are as defined in formula (I), in which process a compound of formula (VI/d):

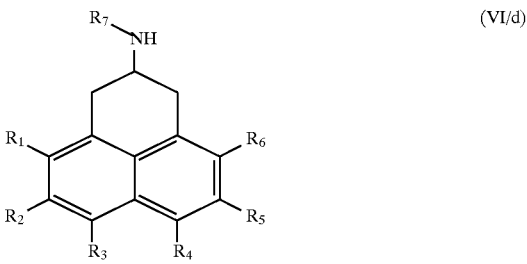 (VI/d)

in which $R_1$, $R_2$, $R_3$, $R_4$, $R_5$, $R_6$ and $R_7$ are as defined above, is reacted either with a compound of formula (VII) or (VIIa):

 (VII)

 (VIIa)

in which $R_{12}$ is as defined in formula (I), the anhydride of formula (VIIa) being mixed or symmetrical, and Hal' represents a halogen, to give a compound of formula (I/d4):

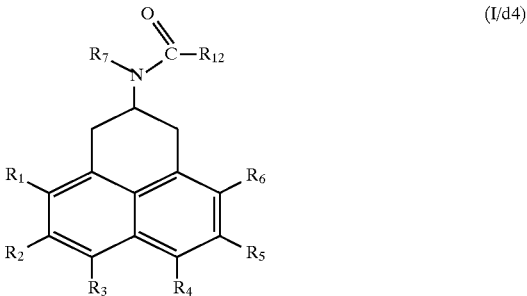 (I/d4)

in which $R_1$, $R_2$, $R_3$, $R_4$, $R_5$, $R_6$, $R_7$ and $R_{12}$ are as defined above, which compound is then subjected to a thionating reagent, such as Lawesson's reagent, to give a compound of formula (I/d4'):

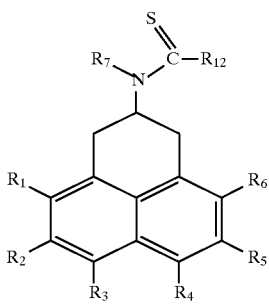
(I/d4')

in which $R_1$, $R_2$, $R_3$, $R_4$, $R_5$, $R_6$, $R_7$ and $R_{12}$ are as defined above, or with a compound of formula (VIII):

 (VIII)

in which $R_{13}$ is as defined in formula (I) and X represents an oxygen or sulfur atom, to give a compound of formula (I/d5):

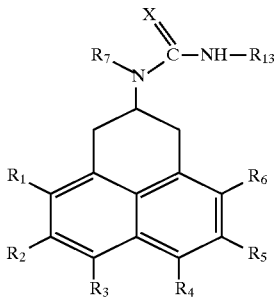
(I/d5)

in which $R_1$, $R_2$, $R_3$, $R_4$, $R_5$, $R_6$, $R_7$, $R_{13}$ and X are as defined above, the compounds of formulae (I/d4), (I/d4') and (I/d5) together forming compounds of formula (I/d), it being possible for the compounds of formula (I/d) thus obtained to be:

purified according to one or more purification methods chosen from crystallization, chromatography on column of silica, extraction, filtration and passage over charcoal or resin, and separated, in pure form or in the form of a mixture, into the possible enantiomers or diastereoisomers thereof.

In general, the compounds of formula (I) in which $R_7$ is other than a hydrogen may be obtained by reacting a corresponding compound of formula (I) in which $R_7$ is a hydrogen, with a compound of formula (V):

 (V)

in which $R_7'$ is as defined in formula (I) and Hal represents a halogen atom.

More particularly, the invention relates to the processes for the preparation of the compounds of formula (I) in which, where appropriate, $R_1$, $R_2$, $R_3$ and $R_4$ and $R_5$, $R_5'$, $R_6$ and $R_6'$ simultaneously represent hydrogens, or in which, where appropriate, one of these substituents $R_1$, $R_2$, $R_3$, $R_4$ and $R_5$, $R_5'$, $R_6$ and $R_6'$ is a radical chosen from halogen, alkyl and alkoxy, for example alkoxy, the other substituents being hydrogen atoms.

For example, the invention relates to the processes for the preparation of the compounds of formula (I/d) in which, where appropriate, $R_1$, $R_2$, $R_3$ and $R_4$ and $R_5$, $R_5'$, $R_6$ and $R_6'$ simultaneously represent hydrogens, or in which, where appropriate, one of these substituents $R_1$, $R_2$, $R_3$ and $R_4$ and $R_5$, $R_5'$, $R_6$ and $R_6'$ is a radical chosen from halogen, alkyl and alkoxy, for example alkoxy, the other substituents being hydrogen atoms.

The invention also relates to the process for the preparation of the compounds of formula (I/i), a specific case of the compounds of formula (I):

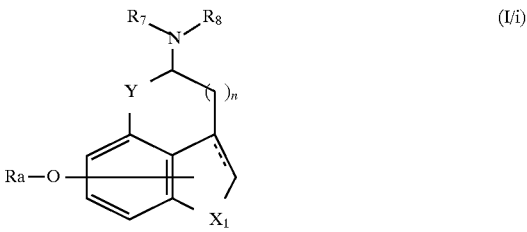
(I/i)

in which $R_7$, $R_8$, Ra, n, $X_1$ and Y are as defined in formula (I), by grafting a radical Ra onto a compound of formula (I/j):

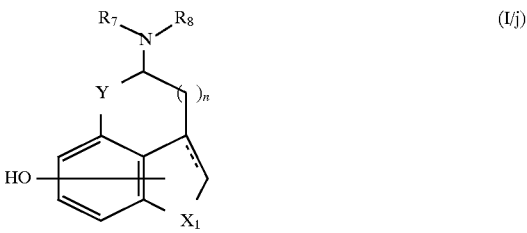
(I/j)

in which $R_7$, $R_8$, $X_1$, Y and n are as defined above, it being possible for the compounds of formula (I/i) thus obtained to be:

purified according to one or more purification methods chosen from crystallization, chromatography on a column of silica, extraction, filtration and passage over charcoal or resin, and separated, in pure form or in the form of a mixture, into the possible enantiomers or diastereoisomers thereof.

For example, the invention also relates to the process for the preparation of compounds of formula (I/i-1), a specific case of the compounds of formula (I-1) as defined above:

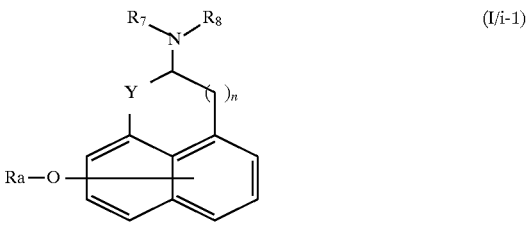
(I/i-1)

in which $R_7$, $R_8$, Ra, n and Y are as defined in formula (I), by grafting a radical Ra onto a compound of formula (I/j-1):

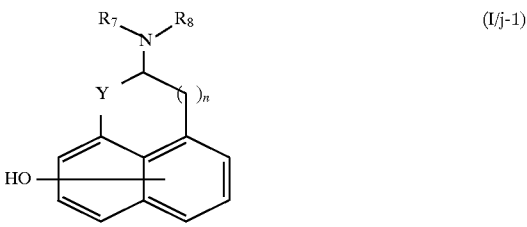
(I/j-1)

in which $R_7$, $R_8$, Y and n are as defined above, it being possible for the compounds of formula (I/i) thus obtained to be:

purified according to one or more purification methods chosen from crystallization, chromatography on a column of silica, extraction, filtration and passage over charcoal or resin, and separated, in pure form or in the form of a mixture, into the possible enantiomers or diastereoisomers thereof.

For example, the radical Ra may be grafted by means of a compound of formula (IX):

  (IX)

in which Ra is as defined in formula (I) and W represents a halogen or a leaving group.

The compounds of formula (I/j):

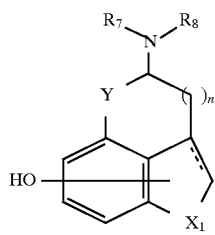 (I/j)

in which $R_7$, $R_8$, $X_1$, Y and n are as defined in formula (I), are accessible to those skilled in the art by dealkylation of a compound of formula (I/k):

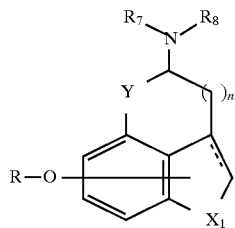 (I/k)

in which $R_7$, $R_8$, n, $X_1$ and Y are as defined above and R represents a ($C_1$–$C_6$)alkyl radical.

For example, the compound (I/k) as defined above may be dealkylated by means of $BBr_3$ or an $AlX'_3/R'$—SH mixture in which X' represents a halogen and R' represents a ($C_1$–$C_6$) alkyl radical.

The compounds of formula (I/j-1):

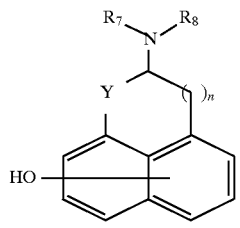 (I/j-1)

in which $R_7$, $R_8$, Y and n are as defined in formula (I), are accessible to those skilled in the art by dealkylation of a compound of formula (I/k-1):

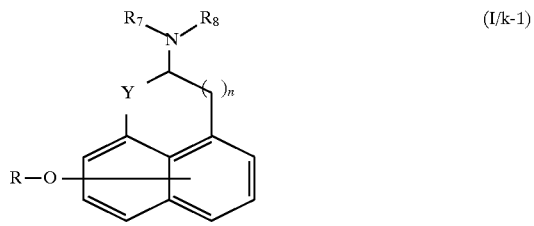 (I/k-1)

in which $R_7$, $R_8$, n and Y are as defined above and R represents a ($C_1$–$C_6$)alkyl radical.

For example, the compound (I/k-1) as defined above may be dealkylated by means of $BBr_3$ or an $AlX'_3/R'$—SH mixture in which X' represents a halogen and R' represents a ($C_1$–$C_6$)alkyl radical.

Each starting material or synthetic intermediate used is purified, if necessary, by means of standard purification methods.

The starting materials used in the above preparation processes are:

either commercial, or accessible to those skilled in the art in the light of the literature or the preparation examples mentioned above.

The compounds of formula (II) are thus accessible by reacting a compound of formula (II/a):

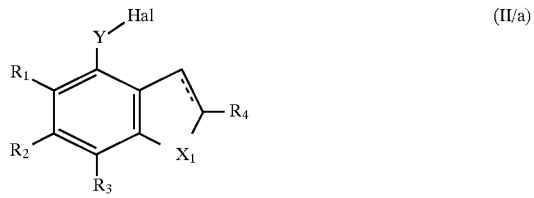 (II/a)

in which $R_1$, $R_2$, $R_3$, $R_4$, $X_1$ and Y are as defined in formula (I) and Hal represents a halogen atom, with a compound of formula (II/b):

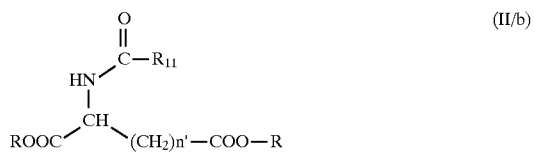 (II/b)

in which $R_{11}$ is as defined in formula (I), n' is 0, 1 or 2, and R represents a ($C_1$–$C_6$)alkyl, to give a compound of formula (II/c):

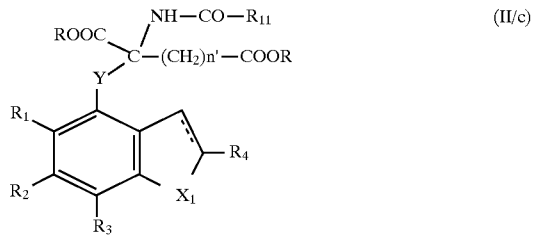 (II/c)

in which $R_1$, $R_2$, $R_3$, $R_4$, $R_{11}$, R, $X_1$, Y and n' are as defined above, which compound is then treated with sodium hydroxide to give the compound of formula (II):

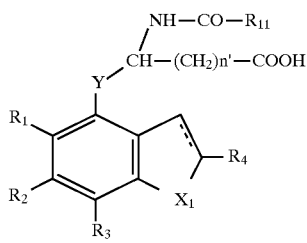

in which $R_1$, $R_2$, $R_3$, $R_4$, $R_{11}$, $X_1$, Y and n' are as defined above.

For example, the compounds of formula (II-1) are thus accessible by reacting a compound of formula (II/a-1):

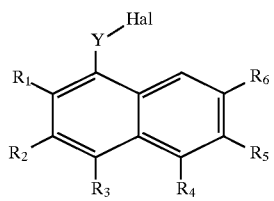

in which $R_1$, $R_2$, $R_3$, $R_4$, $R_5$, $R_6$ and Y are as defined in formula (I) and Hal represents a halogen atom, with a compound of formula (II/b-1):

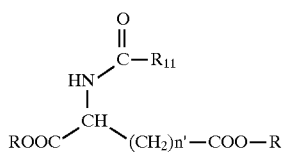

in which $R_{11}$ is as defined in formula (I), n' is 0, 1 or 2 and R represents a $(C_1-C_6)$alkyl, to give a compound of formula (II/c-1):

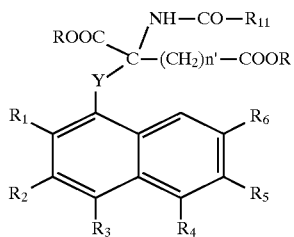

in which $R_1$, $R_2$, $R_3$, $R_4$, $R_5$, $R_6$, $R_{11}$, R, Y and n' are as defined above, which compound is then treated with sodium hydroxide to give the compound of formula (II-1):

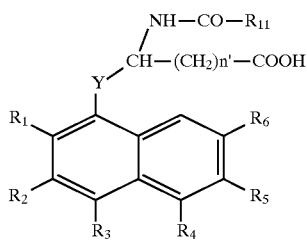

in which $R_1$, $R_2$, $R_3$, $R_4$, $R_5$, $R_6$, $R_{11}$, Y and n' are as defined above.

For example, the compounds of formula (II/d) are thus accessible by reacting a compound of formula (II/d1):

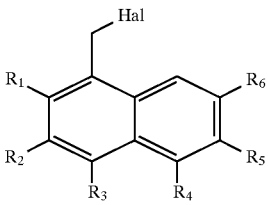

in which $R_1$, $R_2$, $R_3$, $R_4$, $R_5$ and $R_6$ are as defined in formula (I) and Hal represents a halogen atom, with a compound of formula (II/d2):

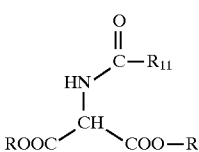

in which $R_{11}$ is as defined in formula (I) and R represents a $(C_1-C_6)$alkyl, to give a compound of formula (II/d3):

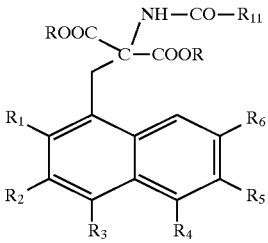

in which $R_1$, $R_2$, $R_3$, $R_4$, $R_5$, $R_6$, $R_{11}$ and R are as defined above, which compound is then treated with sodium hydroxide to give the compound of formula (II/d):

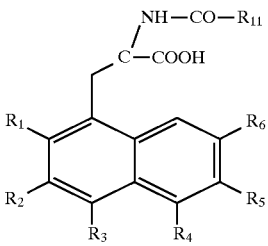

in which $R_1$, $R_2$, $R_3$, $R_4$, $R_5$, $R_6$ and $R_{11}$ are as defined above.

The compounds of formula (VI) as defined above are, for example, accessible by deacylation of a compound of formula (I/g), a specific case of the compounds of formula (I):

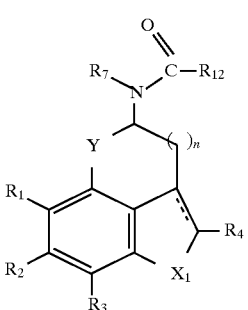

in which $R_1$, $R_2$, $R_3$, $R_4$, $R_7$, $R_{12}$, n, $X_1$ and Y are as defined in formula (I).

The compounds of formula (VI-1) as defined above are, for example, accessible by deacylation of a compound of formula (I/g-1), a specific case of the compounds of formula (I):

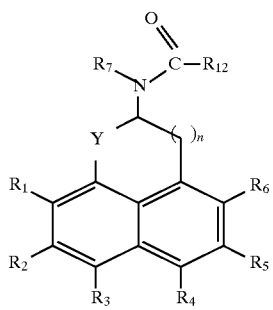

(I/g-1)

in which $R_1$, $R_2$, $R_3$, $R_4$, $R_5$, $R_6$, $R_7$, $R_{12}$, n and Y are as defined in formula (I). For example, the compounds of formula (VI-1) are accessible by deacetylation of a compound of formula (I/h-1):

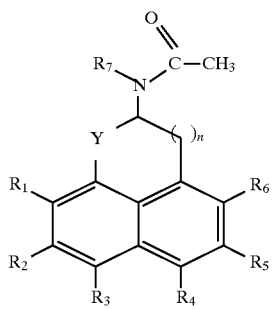

(I/h-1)

in which $R_1$, $R_2$, $R_3$, $R_4$, $R_5$, $R_6$, $R_7$, Y and n are as defined in formula (I).

The compounds of formula (I) possess pharmacological properties which are very advantageous for the clinician.

The compounds of the invention and the pharmaceutical compositions containing them prove to be useful for the treatment of disorders of the melatoninergic system and disorders associated with the melatoninergic system.

Pharmacological study of the derivatives of the invention has in effect shown that they were not toxic, were endowed with a selective, very high affinity for the melatonin receptors and possessed considerable activities on the melatoninergic system in particular; it was noted that they had therapeutic properties on sleeping disorders and anxiolytic, antipsychotic and analgesic properties, as well as microcirculation properties which make it possible to establish that the products of the invention are useful in the treatment of stress, sleeping disorders and anxiety, seasonal depressions, cardiovascular pathologies, insomnia and fatigue due to changes of time zone, schizophrenia, panic attacks, melancholia, appetite disorders, obesity, psoriasis, psychotic disorders, epilepsy, Parkinson's disease, senile dementia, various disorders associated with normal or pathological ageing, migraine, memory losses, Alzheimer's disease and cerebral circulation disorders. In another field of activity, it appears that the products of the invention possess inhibitory properties on ovulation and immunomodulatory properties and that they are capable of being used in anticancer treatment.

The compounds will preferably be used in seasonal depressions, sleeping disorders, cardiovascular pathologies, insomnia and fatigue due to changes of time zone, appetite disorders and obesity.

For example, the compounds will be used in the treatment of seasonal depressions and sleeping disorders.

The subject of the present invention is also the pharmaceutical compositions containing a compound of formula (I) in combination with one or more pharmaceutically acceptable excipients.

Among the pharmaceutical compositions according to the invention, mention may be made more particularly of those suitable for oral, parenteral, nasal, per- or transcutaneous, rectal, perlingual, ocular or respiratory administration and, in particular, simple or coated tablets, sublingual tablets, sachets, packets, gelatin capsules, glossettes, lozenges, suppositories, creams, ointments, dermal gels and drinkable or injectable ampules.

The dosage varies according to the sex, age and weight of the patient, the route of administration, the nature of the therapeutic indication, or any possible combined treatments, and ranges between 0.1 mg et 1 g per 24 hours, more particularly between 1 and 100 mg, for example between 1 and 10 mg.

The examples which follow illustrate the invention without, however, limiting it in any way.

PREPARATION 1

2-ACETAMIDO-3-(1-NAPHTHYL)PROPANOIC ACID

STAGE A: DIETHYL 2-[(1-NAPHTHYL)METHYL]-2-ACETAMIDOMALONATE

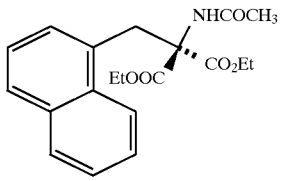

Stage A

Procedure:

Sodium (28 mmol; 0.64 g) is introduced into 50 cm$^3$ of absolute ethanol, under inert atmosphere. At 0° C., diethyl 2-acetamidomalonate (28 mmol; 6.08 g) dissolved in 35 cm$^3$ of absolute ethanol is added, followed by dropwise addition, with a syringe, of (1-naphthyl)methyl chloride (28 mmol; 4.1 cm$^3$). The mixture is maintained at reflux until the starting material has disappeared (6 h, then overnight at room temperature and then 2 h at reflux). The reaction medium is poured onto a KHSO$_4$ (0.05M; 240 cm$^3$)/hexane (120 cm$^3$) mixture and stirred vigorously. A white precipitate, which is the expected malonic derivative, is recovered.

Yield: 79%

$^1$H NMR (CDCl$_3$) δ(ppm): 1.29 (t, 6H, J=7.1 Hz, 2 CH$_2$CH$_3$); 1.87 (s, 3H, COCH$_3$); 4.13 (s, 2H, CH$_2$); 4.17–4.31 (m, 4H, 2 CH$_3$CH$_2$); 6.41 (s, 1H, NH); 7.16 (d, 1H, H$_{ar}$); 7.32–7.41 (m, 3H, H$_{ar}$); 7.73–7.82 (m, 2H, Har); 7.96–8.01 (m, 1H, H$_{ar}$).

STAGE B: 2-ACETAMIDO-3-(1-NAPHTHYL)PROPANOIC ACID

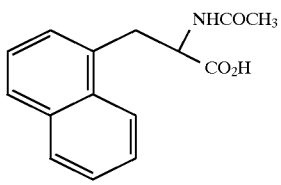

Stage B

Procedure

The malonic derivative obtained in the above stage (7 mmol; 2.5 g) is dissolved in 13 cm$^3$ of ethanol. 2N sodium hydroxide (18 mmol; 9 cm$^3$; 2.5 eq.) is added and the solution is maintained at reflux for 3 h 30 min. The medium is acidified to pH=1 with KHSO$_4$ solution (1N). A precipitate forms, which is filtered off and the title compound is isolated and recrystallized from an acetone/petroleum ether mixture.

Yield: 89%

Thin layer chromatography (TLC) (silica): Rf=0.18 (AcOH:MeOH:$CH_2Cl_2$ 0.5:4.5:95) m.p. (melting point)= 171°–173° C.

$^1$H NMR ($CD_3OD$) δ(ppm): 1.68 (s, 3H, $COCH_3$); 3.08–3.19 (q, 1H, AB of a $CHCH_2$ ABX system); 3.53–3.63 (q, 1H, AB of a $CHCH_2$ ABX system); 4.6–4.65 (m, 1H, CH); 7.19–7.38 (m, 4H, $H_{ar}$); 7.58 (t, 1H, $H_{ar}$); 7.68 (dd, 1H, $H_{ar}$); 7.98 (d, 1H, J=8.3 Hz, $H_{ar}$).

PREPARATION 2

(2,3-DIHYDRO-1H-PHENALEN-2-YL)AMINE

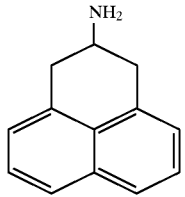

Procedure:

N-(2,3-Dihydro-1H-phenalen-2-yl)acetamide (0.97 mmol; 0.22 g) is solubilized in 2 cm$^3$ of dioxane and 9 cm$^3$ of 10% HCl are added. The mixture is maintained at 100° C. for 3 h and then at 90° C. overnight. After cooling, 10% NaOH is added until the pH is basic and the amine is extracted with $CH_2Cl_2$. The organic phase is dried over $MgSO_4$ and evaporated under reduced pressure. The desired amine is thus isolated without further purification.

Yield: 90%

$^1$H NMR ($CDCl_3$) δ(ppm): 1.7 (bs, 2H, $NH_2$); 2.85–3.0 (q, 2H, AB of a $CHCH_2$ ABX system); 3.2–3.4 (q, 2H, AB of a $CHCH_2$ ABX system); 3.42–3.6 (m, 1H, CH); 7.25 (d, 2H, $H_{ar}$); 7.35 (t, 2H, $H_{ar}$); 7.68 (d, 2H, $H_{ar}$).

PREPARATION 3

2-ACETAMIDO-3-(2-METHOXY-1-NAPHTHYL)PROPANOIC ACID

STAGE A: (2-METHOXY-1-NAPHTHYL) METHYL CHLORIDE

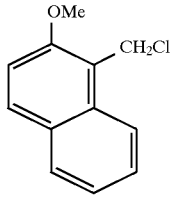

Stage A

Procedure:

To a suspension of lithium aluminum hydride (96.66 mmol; 3.69 g; 3 eq.) in anhydrous tetrahydrofuran (THF) is added dropwise, at 0° C. and under argon, a solution of (2-methoxy-1-naphthyl)carbaldehyde (32.22 mmol; 6 g) in 30 cm$^3$ of the same solvent. Stirring is maintained overnight at room temperature. The mixture is hydrolyzed by slow addition, at 0° C., of 4 cm$^3$ of water followed by 4 cm$^3$ of 15% NaOH solution and finally 12 cm$^3$ of water. The precipitate formed is filtered off; the filtrate is dried over $MgSO_4$ and then evaporated. 2-(2-Methoxy-1-naphthyl)nethanol, which is pure by NMR, is isolated.

The alcohol thus obtained (30.28 mmol; 5.7 g) is dissolved in 80 cm$^3$ of anhydrous toluene in the presence of pyridine (30.28 mmol; 2.5 cm$^3$). Thionyl chloride (72.67 mmol; 5.3 cm$^3$; 2.4 eq.) in solution in 6 cm$^3$ of anhydrous toluene is added dropwise, at 0° C. under an argon atmosphere. Stirring is continued overnight at room temperature and the reaction medium is then poured onto ice and stirred for 1 h. The organic phase is washed with saturated $NaHCO_3$ solution, with saturated NaCl solution and then once with water. It is dried over $MgSO_4$ and then evaporated. The title compound, which is pure by NMR, is isolated.

Yield: 82% TLC (silica): $R_f$=0.8 ($CH_2Cl_2$: pentane)

$^1$H NMR ($CDCl_3$) δ(ppm): 4.0 (s, 3H, $OCH_3$); 5.2 (s, 2H, $ClCH_2$); 7.25 (d, 1H, $H_{ar}$); 7.43 (t, 1H, $H_{ar}$); 7.6 (t, 1H, $H_{ar}$); 7.88 (2d, 2H, $H_{ar}$); 8.08 (d, 1H, $H_{ar}$).

STAGE B: DIETHYL 2-[(2-METHOXY-1-NAPHTHYL)METHYL]-2-ACETAMIDOMALONATE

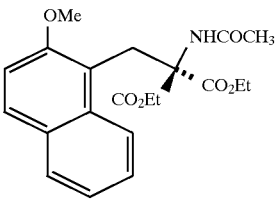

Stage B

Procedure:

Diethyl acetamidomalonate (44.5 mmol; 9.65 g; 1.2 eq.) is dissolved in 60 cm$^3$ of pre-distilled anhydrous dimethylformamide (DMF). Sodium hydride (NaH) (44.5 mmol; 1.78 g of a 60% in oil suspension; 1.2 eq.)is added, at 0° C. under argon. The chloride obtained in the above stage (37 mmol; 7.66 g) in solution in 30 cm$^3$ of anhydrous DMF is subsequently added dropwise and the mixture is then maintained at reflux for 20 h. The DMF is then evaporated off and the residue is taken up in dichloromethane and washed several times with water. The organic phase is dried over $MgSO_4$ and then evaporated under reduced pressure. The light-brown powder obtained is washed with ether and filtered. The title compound is thus obtained.

Yield: 84% TLC (silica): $R_f$=0.15 ($CH_2Cl_2$) m.p.=110° C.

$^1$H NMR ($CDCl_3$) δ(ppm): 1.22 (t, 6H, 2x $CH_2CH_3$); 1.63 (s, 3H, $COCH_3$); 3.78 (s, 3H, $OCH_3$); 4.05 (s, 2H, $CH_2$); 4.16 (q, 4H, 2x $CH_2CH_3$); 6.19, (s, 1H, NH); 7.16 (d, 1H, $H_{ar}$); 7.24 (t, 1H, $H_{ar}$); 7.36 (t, 1H, $H_{ar}$); 7.69 (2d, 2H, $H_{ar}$); 7.89 (d, 1H, $H_{ar}$).

Stage C: 2-(ACETAMIDO)-3-(2-METHOXY-1-NAPHTHYL)PROPANOIC ACID

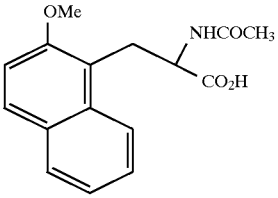

Stage C

Procedure:

The compound obtained in the above stage (21.38 mmol; 8.1 g) is dissolved in 44 cm$^3$ of ethanol to which is added 2N sodium hydroxide (31 cm$^3$). The reaction medium is maintained at reflux for 6 h and the solvent is then evaporated to half its volume. The mixture is extracted once with ether and the aqueous phase is then acidified to pH 1 with 1N $KHSO_4$ solution. A brown deposit appears, and is extracted with ethyl acetate. The organic phase is washed with water, then dried over MgSO$_4$ and then evaporated under reduced pressure. The pure title compound is isolated in the form of a white powder.

Yield: 87% m.p.=201° C.

$^1$H NMR (CD$_3$OD) δ(ppm): 1.88 (s, 3H, COCH$_3$); 3.52–3.77 (m, 2H, AB of a CHCH$_2$ ABX system); 4.04 (s, 3H, OCH$_3$); 4.74–4.78 (q, 1H, CH); 7.36–7.45 (m, 2H, H$_{ar}$); 7.56 (t, 1H, H$_{ar}$); 7.87 (2d, 2H, H$_{ar}$); 8.12 (d, 1H, H$_{ar}$).

PREPARATION 4

(4-METHOXY-2,3-DIHYDRO-1H-PHENALEN-2-YL)AMINE

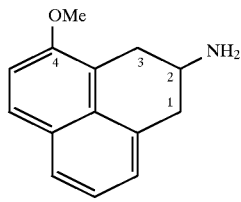

Procedure:

N-(4-Methoxy-2,3-dihydro-1H-phenalen-2-yl)acetamide (5.95 mmol; 1.52 g) is dissolved in 20 cm$^3$ of ethanol to which are added 54 cm$^3$ of 10% HCl. The mixture is maintained at 90° C. for 20 h. After cooling, 10% NaOH solution is added until the pH is basic and the amine is extracted with CH$_2$Cl$_2$. The organic phase is dried over MgSO$_4$ and evaporated under reduced pressure. The title amine is thus isolated without further purification.

Yield: 79%

$^1$H NMR (CDCl$_3$) δ(ppm): 1.6 (s, 2H, NH$_2$); 2.6–2.95 (m, 2H, AB of a CHCH$_2$ ABX system); 3.05–3.45 (m, 3H, X and AB of a CHCH$_2$ ABX system); 3.93 (s, 3H, OCH$_3$); 7.1–7.23 (m, 3H, H$_{ar}$); 7.55 (dd, 2H, H$_{ar}$); 7.65 (d, 1H, H$_{ar}$).

The hydrochloride corresponding to the title amine is obtained by adding ether to a solution of the title amine in a minimum amount of ethanol in the presence of hydrochloric ethanol.

Yield: 80%

$^1$H NMR (CD$_3$OD) δ(ppm): 3.06–3.7 (m, 4H, 2 AB of a CHCH$_2$ ABX system); 3.83–3.9 (m, (CH$_2$)$_2$CH); 4.06 (s, 3H, OCH$_3$); 7.36–7.39 (2d, 2H, H$_{ar}$); 7.49 (d, 1H, H$_{ar}$); 7.79 (t, 1H, H$_{ar}$); 7.9 (d, 1H, H$_{ar}$).

Elemental analysis:
Formula: C$_{14}$H$_{16}$NOCl, M = 249.77

| | | | |
|---|---|---|---|
| Calculated: | C: 67.31% | H: 6.45% | N: 5.60% |
| Found: | C: 67.12% | H: 6.54% | N: 5.66% |

PREPARATIONS 5 TO 32

Working as in Preparation 1, but using a suitably substituted diethyl malonate in Stage A, the following preparations are obtained:

PREPARATION 5
2-PROPIONAMIDO-3-(1-NAPHTHYL) PROPANOIC ACID

PREPARATION 6
2-BUTYRAMIDO-3-(1-NAPHTHYL)PROPANOIC ACID

PREPARATION 7
2-PENTANAMIDO-3-(1-NAPHTHYL) PROPANOIC ACID

PREPARATION 8
2-HEXANAMIDO-3-(1-NAPHTHYL) PROPANOIC ACID

PREPARATION 9
2-HEPTANAMIDO-3-(1-NAPHTHYL) PROPANOIC ACID

PREPARATION 10
2-(2-IODOACETAMIDO)-3-(1-NAPHTHYL) PROPANOIC ACID

PREPARATION 11
2-(2-BROMOACETAMIDO)-3-(1-NAPHTHYL) PROPANOIC ACID

PREPARATION 12
2-TRIFLUOROACETAMIDO-3-(1-NAPHTHYL) PROPANOIC ACID

PREPARATION 13
2-ISOPENTANAMIDO-3-(1-NAPHTHYL) PROPANOIC ACID

PREPARATION 14
2-ISOBUTYRAMIDO-3-(1-NAPHTHYL) PROPANOIC ACID

PREPARATION 15
2-CYCLOPROPYLCARBOXAMIDO-3-(1-NAPHTHYL) PROPANOIC ACID

PREPARATION 16
2-CYCLOBUTYLCARBOXAMIDO-3-(1-NAPHTHYL) PROPANOIC ACID

PREPARATION 17
2-CYCLOHEXYLCARBOXAMIDO-3-(1-NAPHTHYL) PROPANOIC ACID

PREPARATION 18
2-CYCLOPROPYLACETAMIDO-3-(1-NAPHTHYL) PROPANOIC ACID

PREPARATION 19
2-BENZYLCARBOXAMIDO-3-(1-NAPHTHYL) PROPANOIC ACID

PREPARATION 20
2-PHENYLCARBOXAMIDO-3-(1-NAPHTHYL) PROPANOIC ACID

PREPARATION 21
2-ACETAMIDO-3-(4-INDOLYL)PROPANOIC ACID

PREPARATION 22
2-ACETAMIDO-3-(5-METHOXY-4-INDOLYL) PROPANOIC ACID

PREPARATION 23
2-ACETAMIDO-3-(5-BROMO-4-INDOLYL) PROPANOIC ACID

PREPARATION 24
2-ACETAMIDO-3-(5-ETHYL-4-INDOLYL) PROPANOIC ACID

PREPARATION 25
2-ACETAMIDO-3-(4-BENZOFURYL) PROPANOIC ACID

PREPARATION 26

2-ACETAMIDO-3-(5-METHOXY-4-BENZOFURYL) PROPANOIC ACID

PREPARATION 27

2-ACETAMIDO-3-(5-BROMO-4-BENZOFURYL) PROPANOIC ACID

PREPARATION 28

2-ACETAMIDO-3-(5-ETHYL-4-BENZOFURYL) PROPANOIC ACID

PREPARATION 29

2-ACETAMIDO-3-(4-BENZOTHIOPHENYL) PROPANOIC ACID

PREPARATION 30

2-ACETAMIDO-3-(5-METHOXY-4-BENZOTHIOPHENYL) PROPANOIC ACID

PREPARATION 31

2-ACETAMIDO-3-(5-BROMO-4-BENZOTHIOPHENYL) PROPANOIC ACID

PREPARATION 32

2-ACETAMIDO-3-(5-ETHYL-4-BENZOTHIOPHENYL) PROPANOIC ACID

PREPARATION 33

2-ACETAMIDO-3-(2,7-DIMETHOXY-1-NAPHTHYL)PROPANOIC ACID

Stage A: (2,7-dimethoxy-1-naphthyl)methyl chloride 5:

Procedure:

2,7-Dihydroxynaphthalene 1 (62 mmol; 10 g) and dimethyl sulfate (126 mmol; 11.9 cm$^3$) are dissolved in 320 cm$^3$ of anhydrous acetone in the presence of anhydrous K$_2$CO$_3$ (304 mmol; 42 g). The reaction medium is maintained at the reflux temperature of the solvent for 6 h and then at room temperature overnight. After addition of 7.4 cm$^3$ of water, the stirring is continued for a further 2 h at room temperature and the carbonate is then filtered off. The filtrate is dried over MgSO$_4$ and evaporated under reduced pressure. Crystallization from a CH$_2$Cl$_2$: pet. ether mixture allows 10.7 g of expected 2,7-dimethoxynaphthalene 2 to be isolated.

The 2,7-dimethoxynaphthalene 2 (65 mmol; 12.26 g) is dissolved in 150 cm$^3$ of anhydrous dichloromethane under an inert atmosphere. TiCl$_4$ (91 mmol; 10cm$^3$) is added by syringe, at 0° C., followed by dropwise addition, by means of a dropping funnel, of α,α-dichloromethyl methyl ether (99 mmol; 9 cm$^3$) in solution in 40 cm$^3$ of the same solvent. Stirring is continued at 0° C. for 1 h and then at room temperature for 4 h 30. The reaction medium is poured onto an ice/3N HCl mixture (250 cm$^3$), stirred vigorously and then extracted with CH$_2$Cl$_2$. The organic phase is washed with water and then with saturated NaHCO$_3$ solution. The organic phase is dried over MgSO$_4$ and evaporated. The residue is taken up in ether, the solution is filtered and the filtrate is evaporated to dryness. 2,7-Dimethoxynaphthaldehyde 3 is isolated pure in the form of a beige-colored powder.

To a suspension of LAH (46 mmol; 1.75 g) in 100 cm$^3$ of anhydrous THF is added dropwise, at 0° C. under argon, the solution of 2,7-dimethoxynaphthaldehyde 3 (19 mmol; 4 g) in 30 cm$^3$ of the same solvent. Stirring is continued overnight at room temperature. The reaction medium is hydrolyzed by slow addition, at 0° C., of 1.8 cm$^3$ of water, followed by 1.8 cm$^3$ of 15% NaOH solution and finally 5.4 cm$^3$ of water. The precipitate formed is filtered off; the filtrate is dried over MgSO$_4$ and then evaporated. (2,7-Dimethoxynaphthyl)methanol 4, which is pure by NMR, is isolated.

The alcohol 4 (18 mmol; 4 g) is dissolved in 80 cm$^3$ of anhydrous toluene in the presence of pyridine (1.5 cm$^3$). Thionyl chloride (45 mmol; 3.3 cm$^3$; 2.4 eq.) in solution in 3.8 cm$^3$ of the same solvent is added dropwise, at 0° C. under an argon atmosphere. Stirring is continued overnight at room temperature and the reaction medium is then poured onto ice and stirred for 1 h 30. The organic phase is separated out and washed with saturated aqueous NaHCO$_3$ solution, with saturated aqueous NaCl solution and then once with water. It is dried over MgSO$_4$ and then evaporated under reduced pressure. The expected chloride isolated is sufficiently pure to be used directly in reaction.

Physicochemical data:

2:

Yield=91% TLC(silica): Rf=0.83 (CH$_2$Cl$_2$) m.p.=142° C.

$^1$H NMR (CDCl$_3$) δ(ppm): 3.83 (s, 6H, 2xOCH$_3$); 6.90 (dd, 2H, J=9 and 3 Hz, H$_3$ and H$_6$); 7.00 (d, 2H, J=3 Hz, H$_1$ and H$_8$); 7.59 (d, 2H, J=9 Hz, H$_4$ and H$_5$).

3:

Yield=76% TLC (silica): Rf=0.91 (MeOH:CH$_2$Cl$_2$ 5:95) m.p.=98° C.

$^1$H NMR (CDCl$_3$) δ(ppm): 3.91 (s, 3H, OCH$_3$); 3.95 (s, 3H, OCH$_3$); 6.99 (dd, 1H, J=9 and 3 Hz, H$_6$); 7.03 (d, 1H, J=9 Hz, H$_3$); 7.55 (d, 1H, J=9 Hz, H$_5$); 7.87 (d, 1H, J=9 Hz, H$_4$); 8.77 (d, 1H, J=3 Hz, H$_8$); 10.81 (s, 1H, CHO).

4:

Yield=94% m.p.=107° C.

$^1$H NMR (CDCl$_3$) δ(ppm): 1.97–2.02 (bs, 1H, OH); 3.95 (s, 3H, OCH$_3$); 3.97 (s, 3H, OCH$_3$); 5.16 (s, 2H, HOCH$_2$); 7.05 (dd, 1H, J=11 and 3 Hz, H$_6$); 7.13 (d, 1H, J=11 Hz, H$_3$); 7.39 (d, 1H, J=3 Hz, H$_8$); 7.71 (d, 1H, J=11 Hz, H$_4$); 7.76 (d, 1H, J=11 Hz, H$_5$).

5:

Yield=94%

$^1$H NMR (CDCl$_3$) δ(ppm): 3.97 (s, 3H, OCH$_3$); 3.99 (s, 3H, OCH$_3$); 5.16 (s, 2H, ClCH$_2$); 7.05 (dd, 1H, J=9 and 3 Hz, H$_6$); 7.11 (d, 1H, J=9 Hz, H$_3$); 7.28 (d, 1H, J=3 Hz, H$_8$); 7.70 (d, 1H, J=9 Hz, H$_4$); 7.77 (d, 1H, J=9 Hz, H$_5$).

Stage B: diethyl 2-[(2,7-dimethoxy-1-naphthyl) methyl]-2-acetamido-malonate:

Procedure:

Diethyl acetamidomalonate (21 mmol; 4.5 g) is dissolved in 30 cm$^3$ of previously distilled anhydrous DMF. NaH (21 mmol; 0.5 g of a 60% suspension in oil) is added, at 0° C. under argon. The chloride obtained in the above stage (17 mmol; 4.08 g) in solution in 16 cm$^3$ of anhydrous DMF is subsequently added dropwise and the reaction medium is then maintained at the reflux temperature of the solvent for 20 h. The DMF is evaporated off and the residue is taken up in dichloromethane and washed several times with water. The organic phase is dried over MgSO$_4$ and then evaporated under reduced pressure. The product obtained is washed with ether and filtered. The pure derivative of Stage B is thus isolated.

Yield=55% TLC (silica): Rf=0.79 (MeOH:CH$_2$Cl$_2$ 2:98)

$^1$H NMR (CDCl$_3$) δ(ppm): 1.29 (t, 6H J=7 Hz, 2x CH$_2$CH$_3$); 1.65 (s, 3H, COCH$_3$); 3.82 (s, 3H, OCH$_3$); 3.94

(s, 3H, OCH₃); 4.07 (s, 2H, CH₂); 4.17–4.38 (m, 4H, 2x CH₂CH₃); 6.27 (s, 1H, NH); 6.96 (dd, 1H, J=9 and 2.3 Hz, H₆); 7.04 (d, 1H, J=9 Hz, H₃); 7.27 (d, 1H, J=2.3 Hz, H₈); 7.63 (d, 1H, J=9 Hz, H₄); 7.69 (d, 1H, J=9 Hz, H₅).

Stage C: 2-acetamido-3-(2,7-dimethoxy-1-naphthyl) propanoic acid

Procedure:

The compound obtained in the above stage (10 mmol; 4.01 g) is dissolved in 30 cm³ of ethanol to which is added 2N sodium hydroxide (15 cm³). The reaction medium is maintained at the reflux temperature of the solvent for 3 h and at room temperature overnight. The mixture is extracted once with ether and the aqueous phase is then acidified to pH 1 with KHSO₄ solution (1N). The precipitate formed is extracted with ethyl acetate. The organic phase is washed with water, then dried over MgSO₄ and then evaporated under reduced pressure. The expected compound is isolated pure in the form of a white powder.

Yield=76%

¹H NMR (CD₃OD) δ(ppm): 1.83 (s, 3H, COCH₃); 3.40–3.67 (m, 2H, CH₂); 3.9 (s, 6H, 2xOCH₃); 4.63–4.71 (t, 1H, CH); 6.78–6.84 (dd, 1H, J=9 Hz, H$_{ar}$); 7.13 (d, 1H, H$_{ar}$); 7.32 (d, 1H, H$_{ar}$); 7.63 (d, 1H, H$_{ar}$); 7.68 (d, 1H, H$_{ar}$).

PREPARATION 34

2-PROPIONAMIDO-3-(2,7-DIMETHOXY-1-NAPHTHYL) PROPANOIC ACID

PREPARATION 35

2-CYCLOPROPYLCARBOXAMIDO-3-(2,7-DIMETHOXY-1-NAPHTHYL)PROPANOIC ACID

PREPARATION 36

N-ETHYL-N-(4-METHYL-2,3-DIHYDRO-1H-PHENALEN-2-YL)AMINE (J. Chem. Soc 1971, (9), pp. 1607–1609)

PREPARATION 37

N-METHYL-N-(2,3-DIHYDRO-1H-PHENALEN-2-YL)AMINE (Chim. Ther. 1971, 6(3), pp. 196–202)

PREPARATION 38

(5-METHOXY-2,3-DIHYDRO-1H-PHENALEN-2-YL)AMINE (Tetrahedron Lett. 1988, 29(16), pp.1883–1886)

PREPARATION 39

10-METHOXY-2-AMINO-1,2,3,4-TETRAHYDROPHENANTHRENE

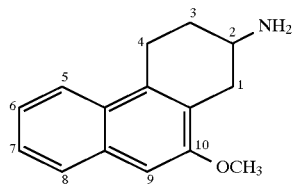

Stage A: methyl 2-methoxy-3-naphthoate

2-Hydroxy-3-naphthoic acid (18.8 g; 100 mmol), dimethyl sulfate (1 eq.) and anhydrous K₂CO₃ (4.8 eq.) in 500 cm³ of anhydrous acetone are maintained at reflux for 6 h. 25 cm³ of water are added to the cooled mixture, which is stirred at room temperaure for 2 h. After filtration, ether is added and the solution is dried over MgSO₄. The solvent is evaporated off to give the compound, which is purified by flash chromatography on silica gel (eluent: ether/petroleum ether). Oil.

Yield: 96%

¹H NMR (200 MHz, CDCl₃) δ8.2 (s, 1H), 7.6–7.65 (2d, J=8.1 Hz, 2H), 7.2–7.35 (2td, J=8.1, 6.9 and 1.1 Hz, 2H), 7.05 (s, 1H); 3.85–3.9 (2s, 6H); ¹³C NMR (200 MHz, CDCl₃); δ166.4, 155.4, 135.8, 132.5, 128.4, 128.1, 127.2, 126.2, 124.6, 121.4, 106.5, 55.6, 51.9.

Stage B: (2-methoxy-naphth-3-yl)methanol

A solution of the compound obtained in the above stage (10.8 g, 50 mmol) is added slowly to a stirred suspension of LiAlH₄ (28.9 mmol) in 50 cm³ of anhydrous THF, cooled to 0° C. by an ice bath. The mixture is brought to room temperature and then maintained at reflux for 18 h with stirring. Water (1 cm³), 15% NaOH solution (1 cm³) and then water (3 cm³) are added dropwise to the cooled mixture until no further evolution of gas is observed. The solution is filtered over MgSO₄ and the solvents are removed under vacuum. The residue is purified by flash chromatography (eluent: 2% methanol/CH₂Cl₂).

Yield: 85.3% m.p.=70.5° C.

¹H NMR (200 MHz, CDCl₃) δ7.55 (m, 3H), 7.1–7.3 (m, 2H), 6.9 (s, 1H), 4.6 (s, 2H); 3.7 (s, 3H); 2.8 (s, 1H) ¹³C NMR (200 MHz, CDCl₃); δ155.7, 133.9, 130.5, 128.6, 127.6, 127.1, 126.3, 126.1, 123.8, 104.9, 61.9, 55.1.

Stage C: 2-methoxy-3-chloromethylnaphthalene

A solution of thionyl chloride (1.5 eq.) and pyridine (1 eq.) in anhydrous toluene (360 cm³) is cooled to 0° C. in an ice bath. The compound obtained in the above stage is added slowly with vigorous stirring.

The medium is stirred at room temperature overnight and then poured onto ice. The solution is stirred for 1 h.

The organic phase is separated out and then washed twice with water, followed by saturated aqueous NaHCO₃ solution and brine. After drying over MgSO₄, the solvent is evaporated off to give the expected compound.

Yield: 98.3% Light-yellow powder m.p.=134° C.

¹H NMR (200 MHz, CDCl₃) δ7.7 (m, 2H), 7.6 (m, 2H), 7.25–7.35 (m, 2H), 7.0 (s, 1H); 4.7 (s, 2H); 3.8 (s, 3H) ¹³C NMR (200 MHz, CDCl₃); δ155.2, 134.4, 129.7, 128.1, 127.5, 127.1, 126.6, 126.2, 123.8, 105.3, 55.3, 41.9.

Stage D: (2-methoxy-3-methylnaphthyl)succinic acid

Sodium (265 mmol) is added portionwise to a solution of diethyl acetylsuccinate (278 mmol) in 200 cm³ of anhydrous toluene and heated to 80° C. The compound obtained in the above stage (316 mmol) is added slowly and the reaction medium is maintained at reflux for 18 h. The cooled solution is acidified with acetic acid to pH 7 and evaporated.

Water is added and the solution is extracted with ether. The combined organic phases are dried over MgSO₄ and the solvent is removed to give a residue which is hydrolyzed by boiling it in 1400 cm³ of 2N NaOH for 18 h. The cooled alkaline solution is washed with ether and acidified with concentrated HCl in order to obtain the title compound in the form of an oil, which is extracted with ethyl acetate. The organic phase is dried over MgSO₄ and the solvent is evaporated off. The product is recrystallized from acetone/toluene.

Yield: 16% m.p.=159° C.

¹H NMR (200 MHz, CD₃OD) δ7.75–7.8 (m, 2H), 7.6 (s, 1H), 7.3–7.5 (m, 2H); 7.3 (s, 1H), 4.0 (s, 3H), 3.2–3.4 (m, 2H), 3.0 (m, 1H), 2.4–2.75 (m, 2H); ¹³C NMR (200 MHz, CD₃OD); δ178.6, 175.9, 157.8, 135.6, 130.9, 130.2, 129.9, 128.3, 127.6, 127.1, 34.2, 124.8, 106.3, 55.9, 42.9, 36.4.

Stage E: 10-methoxy-2-carboxy-1,2,3,4-tetrahydrophenanthren-4-one

The compound obtained in the above stage (33.6 mmol) is converted into the anhydride by refluxing it with acetic anhydride (80 g) for 2 h. The solvent is removed under vacuum to give a brown oil, which is used without further purification.

The anhydride thus obtained (25.5 mmol) is dissolved in 60 cm³ of nitrobenzene and is added slowly to a solution of AlCl₃ (75.5 mmol) in 60 m³ of nitrobenzene at 0° C. The reaction mixture is stirred for 5 min and a solution of ice with 40 cm³ of concentrated HCl is added. The mixture is left to stand overnight and the nitrobenzene is then removed by vapor training. The cooled solution is extracted with ethyl acetate and the organic phase is dried over MgSO₄, then the solvent is evaporated off. The title product is purified by flash chromatography on silica gel (eluent: 5% methanol/CH₂Cl₂).

Yield: 58% m.p.=196° C.

¹H NMR (200 MHz, CD₃OD) δ9.1 (m, 1H), 7.6 (m, 1H), 7.35 (m, 2H); 7.2 (s, 1H), 3.8 (s, 3H), 2.8–3.4 (m, 5H); ¹³C NMR (200 MHz, CD₃OD); δ200.6, 177.0, 155.7, 138.8, 135.2, 129.4, 128.9, 128.4, 127.7, 127.5, 127.2, 112.7, 56.4, 43.4, 40.2, 27.7.

Stage F: 10-methoxy-2-carboxy-1,2,3,4-tetrahydrophenanthrene

The compound obtained in the above stage (11.1 mmol) is reduced with H₂ at atmospheric pressure, using activated palladium-on-charcoal as catalyst. The reaction is performed overnight with 10% by weight of 10% Pd/C in AcOH at 70° C.

Yield: 83% m.p.=235° C.

¹H NMR (200 MHz, CDCl₃) δ7.8 (dd, J=7.3, 2.2 Hz, 1H), 7.6 (dd, J=7, 2.2 Hz, 1H), 7.3 (m, 2H) 6.9 (s, 1H), 3.8 (s, 3H), 2.5–3.3 (m, 5H), 2.25 (m, 1H), 1.8 (m, 1H); ¹³C NMR (200 MHz, CDCl₃); δ178.4, 155.6, 132.8, 132.0, 127.4, 126.9, 125.3, 125.2, 123.3, 122.5, 102.5, 54.9, 39.0, 26.2, 25.2, 25.1.

Stage G: 10-methoxy-2-amino-1,2,3,4-tetrahydrophenanthrene

A solution of the compound obtained in the above stage (7.5 mmol), diphenylphosphoryl azide (1 eq.) and triethylamine (1.1 eq.) in 35 cm³ of tert-butanol is maintained at reflux for 18 h. The reaction mixture is evaporated, 220 cm³ of toluene are added and the solution is washed successively with 5% citric acid solution (20 cm³), water (20 cm³), saturated aqueous NaHCO₃ solution (40 cm³) and brine (20 cm³). The solvent is removed under vacuum to give the corresponding carbamate derivative, which is used without further purification.

To a solution of the carbamate (1.1 mmol) in 10 cm³ of ethyl acetate are added 10 cm³ of hydrochloric ethyl acetate solution in anhydrous ethyl acetate. The reaction medium is stirred for 3 h and then evaporated to give the title compound, which is purified by dissolving it in ethanol and then precipitating it from diethyl ether. The precipitate is filtered off and dried to give the title compound in the form of the hydrochloride.

Yield: 77% m.p.=272° C. (hydrochloride)

¹H NMR (200 MHz, CD₃OD) δ7.6 (d, J=7.3 Hz, 1H), 7.5 (J=8.7 Hz, 1H), 7.2–7.1 (m, 2H), 6.9 (s, 1H), 3.7 (s, 3H), 3.3 (m, 1H) 3.2–3.0 (m, 2H) 3.0–2.8 (m, 1H), 2.5 (m, 1H), 2.15 (m, 1H), 1.8–1.7 (m, 1H); ¹³C NMR (200 MHz, CD₃OD); δ156.5, 134.7, 132.3, 128.5, 128.2, 126.8, 124.8, 123.6, 123.5, 104.4, 55.7, 48.9, 29.3, 27.7, 25.0.

PREPARATION 40

10-METHOXY-3-AMINO-1,2,3,4-TETRAHYDROPHENANTHRENE

Working as in Preparation 39, but starting with suitably substituted naphthoic acid, the title product is obtained.

PREPARATION 41

9-METHOXY-2-AMINO-1,2,3,4-TETRAHYDROANTHRACENE

Working as in Preparation 39, but starting with 1-hydroxy-2-naphthoic acid, the title product is obtained.

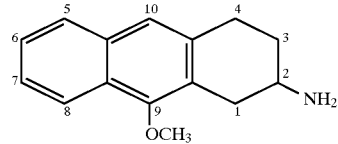

Stage A: methyl 1-methoxynaphthoate

Yield: 95% oil.

Stage B: 1-methoxy-2-hydroxymethylnaphthalene

Yield: 84.3% m.p.: 68° C.

Stage C: 1-methoxy-2-chloromethylnaphthalene

Yield: 98% m.p.: 134° C.

Stage D: (1-methoxy-2-methylnaphthyl)succinic acid

Yield: 17% m.p.: 161° C.

Stage E: 10-methoxy-3-carboxy-1,2,3,4-tetrahydroanthracen-1-one

Yield: 46.3% m.p.: 202° C.

Stage F: 9-methoxy-2-carboxy-1,2,3,4-tetrahydroanthracene

NB: The reduction is carried out in methanol in the presence of HCl. After filtration, the oil should be hydrolyzed by boiling it with 2N NaOH for 30 min followed by acidification with concentrated HCl to pH 1, to give the title product.

Yield: 61% m.p.: 192° C.

Stage G: 9-methoxy-2-amino-1,2,3,4-tetrahydroanthracene

Yield: 45% m.p.: 285° C. (hydrochloride)

EXAMPLE 1

N-(2,3-DIHYDRO-1H-PHENALEN-2-YL) ACETAMIDE

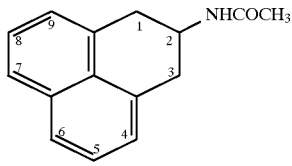

Stage A: 2-methyl4-[(naphth-1-yl)methyl]oxazolin-5-one

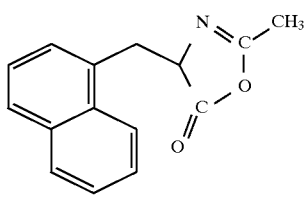

Procedure:

The compound obtained in Preparation 1 (28.76 mmol; 7.4 g) is dissolved in 10 eq. of $Ac_2O$ (287.6 mmol; 27.18 cm$^3$). The mixture is maintained at reflux for 40 min and the acetic acid is evaporated to dryness. The residue is purified by bulb-oven distillation to give a yellow oil corresponding to the title compound.

Yield: 89% TLC (silica): $R_f$=0.85 (MeOH:$CH_2Cl_2$ 2:98) b.p.=180°–190° C./5 mmHg $^1$H NMR (CDCl$_3$) δ(ppm): 1.42 (s, 3H, CH$_3$); 3.32–3.45 (q, 1H, AB of a CHCH$_2$ ABX system); 3.72–3.85 (q, 1H, AB of a CHCH$_2$ ABX system); 3.9–4.12 (m, 1H, CH); 7.4–7.58 (m, 5H, H$_{ar}$); 7.72–7.9 (m, 2H, H$_{ar}$); 8.1 (d, 1H, H$_{ar}$)

Stage B: N-(1-oxo-2,3-dihydro-1-H-phenalen-2-yl) acetamide

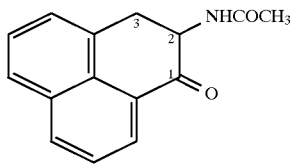

Procedure:

To a solution of AlCl$_3$ (45.75 mmol; 6.1 g; 3 eq.) in 75 cm$^3$ of Cl$_2$CHCHCl$_2$ is added dropwise the compound obtained in the above stage (15.25 mmol; 3.65 g) in solution in 150 cm$^3$ of the same solvent. The mixture is maintained at 60° C. for 2 h and is allowed to cool to room temperature. The reaction medium is poured onto an ice (25 g)/conc. HCl (1.5 cm$^3$) mixture and stirred for 1 h. The aqueous phase is extracted twice with chloroform and the combined organic phases are then dried over MgSO$_4$ and evaporated under reduced pressure. The residue is chromatographed on a column of silica gel (particle size 60–200 μm), eluent: CH$_2$Cl$_2$ then CH$_2$Cl$_2$:MeOH,98:2,v/v. The title product is thus isolated.

Yield: 54% TLC (silica): $R_f$=0.68 (MeOH:CH$_2$Cl$_2$, 5:95) m.p.=185°–186° C. (CH$_2$Cl$_2$/pet. ether)

$^1$H NMR (CDCl$_3$) δ(ppm): 2.14 (s, 3H, COCH$_3$); 3.09–3.23 (q, 1H, J$_{AX}$=13 Hz, J$_{AB}$=–15 Hz, AB of a CHCH$_2$ ABX system); 4.02–4.13 (q, 1H, J$_{BX}$=5.5 Hz, J$_{AB}$=15 Hz, AB of a CHCH$_2$ ABX system); 4.99–5.05 (m, 1H, CH); 6.48 (bs, 1H, NH); 7.5–7.65 (m, 3H, H$_{ar}$); 7.80–7.84 (m, 1H, H$_{ar}$); 8.1–8.17 (d and t, 2H, H$_{ar}$).

$^{13}$C NMR (CDCl$_3$) δ(ppm): 23.24 (COCH$_3$); 35.19 (CH$_2$); 55.47 (CHNH); 125.52 (C$_{ar}$); 126.49 (C$_{ar}$); 126.62 (C$_{ar}$); 128.96 (C$_{ar}$); 131.04 (C$_{ar}$); 133 (C$_{ar}$); 134.54 (C$_{ar}$); 170.29 (COCH$_3$); 195 (CO)

| Elemental analysis: Formula: $C_{15}H_{13}NO_2$, M = 239.25 | | | |
|---|---|---|---|
| Calculated: | C: 75.29% | H: 5.47% | N: 5.85% |
| Found: | C: 75.03% | H: 5.73% | N: 5.79% |

Stage C: N-(2,3-dihydro-1-H-phenalen-2-yl) acetamide

Procedure:

The ketone obtained in the above stage (2.08 mmol, 0.5 g) is dissolved in 35 cm$^3$ of acetic acid and, after flushing several times with argon, 10% Pd/C (0.25 g) is added and the reaction medium is placed under an H$_2$ atmosphere. Stirring is maintained for 5 h at room temperature and the palladium is filtered off over Celite. The acetic acid is evaporated to dryness and the residue is chromatographed on a column of silica gel (particle size 60–200 μm); eluent: CH$_2$Cl$_2$:MeOH 98:2 v/v. The title compound is thus isolated as well as the N-(1-hydroxy-2,3-dihydro-1H-phenalen-2-yl)acetamide.

N-(2,3-dihydro-1H-phenalen-2-yl)acetamide

Yield: 30% (The yield is 76% after reaction for 21 h under the same conditions) TLC (silica): $R_f$=0.73 (MeOH:CH$_2$Cl$_2$ 5:95) m.p.=180°–181° C. (CH$_2$Cl$_2$/petroleum ether)

$^1$H NMR (CDCl$_3$) δ(ppm): 1.86 (s, 3H, COCH$_3$); 3.06–3.16 (q, 1H, J$_{AX}$=6 Hz, J$_{AB}$=–16 Hz, AB of a CHCH$_2$ ABX system); 3.32–3.42 (q, 1H, J$_{BX}$=3.5 Hz, J$_{AB}$=–15.9 Hz, AB of a CHCH$_2$ ABX system); 4.63–4.73 (m, 1H, CH); 5.6 (bs, 1H, NH); 7.24 (d, 2H, J=7 Hz, H$_{ar}$); 7.41 (t, 2H, J=7 Hz, H$_{ar}$); 7.72 (d, 2H, J=8.3 Hz, H$_{ar}$).

$^{13}$C NMR (CDCl$_3$) δ(ppm): 23.28 (COCH$_3$); 36.31 (2 CH$_2$); 43.95 (CHNH); 125.27 (C$_{ar}$); 125.68 (C$_{ar}$); 126.34 (C$_{ar}$); 132.41 (C$_{ar}$); 169.68 (COCH$_3$).

| Elemental analysis: Formula: $C_{15}H_{15}NO$, M = 225.27 | | | |
|---|---|---|---|
| Calculated: | C: 79.9% | H: 6.71% | N: 6.21% |
| Found: | C: 78,54% | H: 6.85% | N: 6.12% |

N-(1-hydroxy-2,3-dihydro-1H-phenalen-2-yl)acetamide

Yield: 55% TLC (silica): Rf=0.43 (MeOH:CH$_2$Cl$_2$ 5:95) m.p.=205°–206° C.

EXAMPLE 2

N-(4-METHOXY-2,3-DIHYDRO-1H-PHENALEN-2-YL)ACETAMIDE

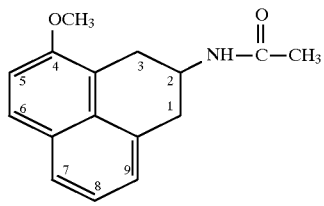

Stage A: 2-methyl-4-[(2-methoxy-naphth-1-yl)methyl]oxazolin-5-one

Procedure:

The compound obtained in Preparation 3 (11.11 mmol; 4 g) is dissolved in 14 cm$^3$ of acetic anhydride and the reaction medium is maintained at reflux for 40 min. The excess anhydride is evaporated to dryness with a trolley pump in order to isolate the title compound, which is used without further purification.

$^1$H NMR (CDCl$_3$) δ(ppm): 2.1 (s, 3H, CH$_3$); 3.55–3.60 (m, 2H, AB of a CHCH$_2$ ABX system); 3.88 (s, 3H, OCH$_3$); 4.42–4.51 (q, 1H, CH); 7.18–7.30 (m, 2H, H$_{ar}$); 7.42 (t, 1H, H$_{ar}$); 7.72 (2 d, 2H, H$_{ar}$); 7.83 (d, 1H, H$_{ar}$).

Stage B: N-(4-methoxy-1-oxo-2,3-dihydro-1H-phenalen-2-yl) acetamide

Procedure:

50 cm3 Cl$_2$CHCHCl$_2$ and aluminum chloride (42.35 mmol; 6 g) are introduced into a three-necked flask placed under an inert atmosphere, followed by dropwise addition of the compound obtained in the above stage dissolved in 90 cm$^3$ of the same solvent. The reaction medium is maintained at 60° C. for 2 h and is then poured onto a water (17 g)/conc. HCl (1.1 cm$^3$) mixture and stirred for 1 h. The organic phase is recovered and the aqueous phase is extracted several times with CH$_2$Cl$_2$. The combined organic phases are dried over MgSO$_4$ and then evaporated. The title compound is purified by chromatography on a column of silica gel (particle size 60–200 μm); eluent: pet. ether:CH$_2$Cl$_2$ 60:30, CH$_2$Cl$_2$ then CH$_2$Cl$_2$:MeOH 99:1 v/v.

Overall yield: 25% TLC (silica): R$_f$=0.8 (CH$_2$Cl$_2$:MeOH 95:5)

$^1$H NMR (CDCl$_3$) δ(ppm): 2.07 (s, 3H, COCH$_3$); 2.61–2.76 (q, 1H, J$_{AX}$=13.2 Hz, J$_{AB}$=16 Hz, AB of a CHCH$_2$ ABX system); 3.9 (s, 3H, OCH$_3$); 4.2–4.32 (q, 1H, J$_{BX}$=7 Hz, J$_{AB}$=16 Hz, AB of a CHCH$_2$ ABX system); 4.84–4.97 (m, 1H CH); 6.75 (d, 1H, NH); 7.25 (d, 1H, J=9 Hz, H$_{ar}$); 7.35 (t, 1H, J=8 Hz, H$_{ar}$); 7.75 (2 d, 2H, J=9 Hz, H$_{ar}$); 8.02 (d, 1H, J=7 Hz, H$_{ar}$).

Optimisation:

The acetamido acid obtained in stage C of the preparation 3 (5.22 mmol; 1.5 g) is suspended in anhydrous CH$_2$Cl$_2$. Oxalyl chloride (5.22 mmol, 0.455 cm$^3$) at −10° C. then 3 to 4 drops of DMF are added.

The product is solubilized and the solution turned yellow. The temperature is maintained at −10° C. for 2 h. AlCl$_3$ (4 eq.; 0.88 mmol; 2.78 g) is quickly added and the solution became dark red. Stirring is strictly maintained at −10° C. for 3 h30. the reaction mixture is poured on a mixture water/ice/con. HCl (0.5 cm$^3$) and then is vigourously stirred. Phases are separed out and the organic phase is washed twice with water then with a NaOH (1N) solution. Aqueous phase is washed several times with dichloromethane then the collected organic phases are dried over MgSO$_4$ and evaporated. The isolated orange powder is taken up in acetone and filtrated (the filtrate may be evaporated, taken up with a minimum acetone and ether in order to optimaze yield). The title product is used without any other purification.

Yield: 50%

Stage C: N-(4-methoxy-2,3-dihydro-1H-phenalen-2-yl)acetamide

Procedure:

The compound obtained in the above stage (3.71 mmol; 1 g) is dissolved in 85 cm$^3$ of acetic acid and, after flushing several times with argon, 10% Pd/C (0.74 g) is added and the reaction medium is placed under an H$_2$ atmosphere. Stirring is maintained for 28 h at room temperature and the palladium is filtered off over celite. The acetic acid is evaporated to dryness and the residue is purified by chromatography on a column of silica gel (particle size 60–200 μm); eluent: CH$_2$Cl$_2$:MeOH 99:1 v/v. The pure title compound is isolated in the form of a white powder.

Yield: 76% TLC (silica): R$_f$=0.74 (CH$_2$Cl$_2$:MeOH 95:5) m.p.=196°–197° C.

$^1$H NMR (CDCl$_3$) δ(ppm): 1.86 (s, 3H, COCH$_3$); 3.01–3.34 (m, 4H, 2 AB of CHCH$_2$ ABX systems); 3.93 (s, 3H, OCH$_3$); 4.62–4.71 (m, 1H, CH); 5.5 (d, 1H, NH); 7.19–7.3 (m, 3H, H$_{ar}$); 7.65 (dd, 2H, J=7 Hz, H$_{ar}$); 7.73 (d, 1H, J=9 Hz, H$_{ar}$).

| Elemental analysis: Formula: C$_{16}$H$_{17}$NO$_2$, M = 225.3 | | | |
|---|---|---|---|
| Calculated: | C: 75.26% | H: 6.71% | N: 5.48% |
| Found: | C: 75.14% | H: 6.72% | N: 5.53% |

EXAMPLE 3

N-(4-METHOXY-2,3-DIHYDRO-1H-PHENALEN-2-YL)PROPIONAMIDE

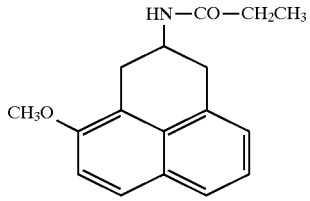

Procedure:

The compound obtained in Preparation 4 (0.56 mmol; 0.120 g) is dissolved in 5 cm$^3$ of dichloromethane in the presence of triethylamine (0.84 mmol; 0.118 cm$^3$; 1.5 eq.) and propanoyl chloride. Stirring is maintained for 40 min at room temperature. The medium is washed twice with water and the organic phase is then dried over MgSO$_4$ and evaporated. The residue is chromatographed on a column of silica gel (particle size 60–200 μm); (eluent: CH$_2$Cl$_2$ then CH$_2$Cl$_2$:MeOH 95:5 v/v) to give the pure title compound.

Yield: 66% TLC (silica): R$_f$=0.81 (MeOH:CH$_2$Cl$_2$ 5:95) m.p.=184°–186° C. (CH$_2$Cl$_2$/Et$_2$O)

$^1$H NMR (CDCl$_3$) δ(ppm): 1.07 (t, 3H, J=7.6, CH$_3$CH$_2$); 2.03 (q, 2H, J=7.6 Hz, CH$_2$CH$_3$); 3.03–3.35 (m, 4H, 2 AB of a CHCH$_2$ ABX system); 3.93 (s, 3H, OCH$_3$); 4.65–4.68 (m, 1H, CH); 5.45 (d, 1H, NH); 7.18–7.29 (m, 3H, H$_{ar}$); 7.65 (d, 1H, J=7.5 Hz, H$_{ar}$); 7.73 (d, 1H, J=9 Hz, H$_{ar}$).

NMR $^{13}$C (CDCl$_3$) δ(ppm): 9.79 (CH$_3$CH$_2$); 29.66 and 29.74 (CH$_2$CH$_3$ and C$_1$) 36.12 (C$_3$); 43.28 (C$_2$); 56.16 (OCH$_3$); 112.91, 117.24, 123.44, 125.72, 126.26, 127.28, 128.44, 130.2, 131.52, 153.78 (C$_{ar}$), 177.22 (CO).

| Elemental analysis: Formula: C$_{17}$H$_{19}$NO$_2$, M = 269.32 | | | |
|---|---|---|---|
| Calculated: | C: 75.8% | H: 7.11% | N: 5.19% |
| Found: | C: 75.72% | H: 7.06% | N: 5.14% |

EXAMPLES 4 TO 19

Working as in Example 1, but starting with Preparations 5 to 20, the compounds of the following examples are obtained:

EXAMPLE 4

N-(2,3-DIHYDRO-1H-PHENALEN-2-YL) PROPIONAMIDE

Second procedure:

To a solution of the amine from Preparation 2 (0.7 mmol; 140 mg) in 7 cm$^3$ of anhydrous CH$_2$Cl$_2$ in the presence of Et$_3$N (1 mmol; 0.16 cm$^3$) is added, at 0° C., propionyl chloride (0.8 mmol; 0.07 cm$^3$). Stirring is maintained for 1 h at room temperature and the medium is then washed twice with water. The organic phase is dried over MgSO$_4$ and then evaporated. The residue is washed with ether and the precipitate is filtered off to give 70 mg of the pure expected product.

Yield: 39% TLC (silica): Rf=0.72 (MeOH:CH$_2$Cl$_2$ 5:95) m.p.=148° C.

$^1$H NMR (CDCl$_3$) δ(ppm): 1.06 (t, 3H, CH$_2$CH$_3$); 2.06 (q, 2H, CH$_2$CH$_3$); 3.05–3.16 (dd, 2H, J$_{AX}$=6 Hz, J$_{AB}$=−16 Hz, AB of ABX systems); 3.33–3.42 (dd, 2H, J=8 Hz, H$_4$ et H$_9$); 7.39 (t, 2H, J=9 Hz, H$_8$ and H$_5$); 7.71 (d, 2H, J=9 Hz, H$_6$ and H$_7$).

| Elemental analysis: Formula: C$_{16}$H$_{17}$NO M = 239.41 | | | |
|---|---|---|---|
| | C % | H % | N % |
| Calculated | 80.29 | 7.16 | 5.85 |
| Found | 72.17 | 6.88 | 5.53 |

EXAMPLE 5

N-(2,3-DIHYDRO-1H-PHENALEN-2-YL) BUTYRAMIDE

EXAMPLE 6

N-(2,3-DIHYDRO-1H-PHENALEN-2-YL) PENTANAMIDE

EXAMPLE 7

N-(2,3-DIHYDRO-1H-PHENALEN-2-YL) HEXANAMIDE

EXAMPLE 8

N-(2,3-DIHYDRO-1H-PHENALEN-2-YL) HEPTANAMIDE

EXAMPLE 9

N-(2,3-DIHYDRO-1H-PHENALEN-2-YL)-2-IODOACETAMIDE

EXAMPLE 10

N-(2,3-DIHYDRO-1H-PHENALEN-2-YL)-2-BROMOACETAMIDE

EXAMPLE 11

N-(2,3-DIHYDRO-1H-PHENALEN-2-YL) TRIFLUOROACETAMIDE

EXAMPLE 12

N-(2,3-DIHYDRO-1H-PHENALEN-2-YL) ISOPENTANAMIDE

EXAMPLE 13

N-(2,3-DIHYDRO-1H-PHENALEN-2-YL) ISOBUTYRAMIDE

EXAMPLE 14

N-(2,3-DIHYDRO-1H-PHENALEN-2-YL) CYCLOPROPYLCARBOXAMIDE

EXAMPLE 15

N-(2,3-DIHYDRO-1H-PHENALEN-2-YL) CYCLOBUTYLCARBOXAMIDE

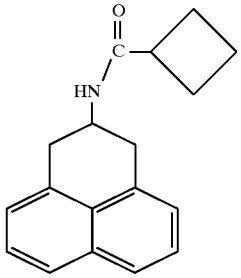

Second procedure:
To a solution of the amine from Preparation 2 (2 mmol, 350 mg) in 7 cm$^3$ of anhydrous CH$_2$Cl$_2$ in the presence of Et$_3$N (0.4 cm$^3$; 1.5 eq.) is added, at 0° C., cyclobutylcarboxylic acid chloride (2 mmol; 0.24 cm$^3$). Stirring is maintained for 1 h at room temperature and the medium is then washed twice with water. The organic phase is dried over MgSO$_4$ and then evaporated. The residue is purified by chromatography on a column of silica gel (particle size 60–200 μm); eluent CH$_2$Cl$_2$:MeOH 99:1. The expected compound is isolated and recrystallized from a CH$_2$Cl$_2$:petroleum ether mixture to give 200 mg of the pure expected amide.

Yield: 40% TLC (silica): Rf=0.89 (MeOH:CH$_2$Cl$_2$ 5:95) m.p.=173° C.

$^1$H NMR (CDCl$_3$) δ(ppm): 1.79–2.25 (m, 6H, 3xCH$_2$); 2.77–2.86 (m, 1H, CH); 3.03–3.14 (dd, 2H, J$_{AX}$=6 Hz, J$_{AB}$=–16 Hz, AB of an ABX system); 3.33–3.42 (dd, 2H, J$_{BX}$=4 Hz, J$_{AB}$=–1 Hz, AB of an ABX system); 4.65–4.69 (m, 1H CH); 5.29–5.42 (s, 1H, NH); 7.24 (d, 2H, J=7 Hz, H$_4$ and H$_9$); 7.4 (t, 2H, J=9 Hz, H$_5$ and H$_8$); 7.71 (d, 2H, J=9 Hz, H$_6$ and H$_7$).

Elemental analysis:
Formula: C$_{18}$H$_{19}$NO
M = 265.34

|  | C % | H % | N % |
|---|---|---|---|
| Calculated | 81.47 | 7.22 | 5.28 |
| Found | 79.35 | 7.35 | 5.09 |

EXAMPLE 16
N-(2,3-DIHYDRO-1H-PHENALEN-2-YL) CYCLOHEXYLCARBOXAMIDE

EXAMPLE 17
N-(2,3-DIHYDRO-1H-PHENALEN-2-YL) CYCLOPROPYLACETAMIDE

EXAMPLE 18
N-(2,3-DIHYDRO-1H-PHENALEN-2-YL) BENZYLCARBOXAMIDE

EXAMPLE 19
N-(2,3-DIHYDRO-1H-PHENALEN-2-YL) PHENYLCARBOXAMIDE

EXAMPLES 20 TO 25

Working as in Example 3, but using the appropriate acyl chloride, the compounds of the following examples are obtained:

EXAMPLE 20
N-(4-METHOXY-2,3-DIHYDRO-1H-PHENALEN-2-YL)ISOBUTYRAMIDE

EXAMPLE 21
N-(4-METHOXY-2,3-DIHYDRO-1H-PHENALEN-2-YL)BUTYRAMIDE

EXAMPLE 22
N-(4-METHOXY-2,3-DIHYDRO-1H-PHENALEN-2-YL)HEXANAMIDE

EXAMPLE 23
N-(4-METHOXY-2,3-DIHYDRO-1H-PHENALEN-2-YL)TRIFLUOROACETAMIDE

EXAMPLE 24
N-(4-METHOXY-2,3-DIHYDRO-1H-PHENALEN-2-YL)CYCLOBUTYLCARBOXAMIDE

EXAMPLE 25
N-(4-METHOXY-2,3-DIHYDRO-1H-PHENALEN-2-YL)CYCLOPROPYLCARBOXAMIDE

EXAMPLES 26 TO 36

Working as in Example 3, but replacing the propanoyl chloride by the appropriate isocyanate or isothiocyanate, the compounds of the following examples are obtained:

EXAMPLE 26
N-(4-METHOXY-2,3-DIHYDRO-1H-PHENALEN-2-YL)-N'-METHYLUREA

EXAMPLE 27
N-(4-METHOXY-2,3-DIHYDRO-1H-PHENALEN-2-YL)-N'-ETHYLUREA

EXAMPLE 28
N-(4-METHOXY-2,3-DIHYDRO-1H-PHENALEN-2-YL)-N'-PROPYLUREA

EXAMPLE 29
N-(4-METHOXY-2,3-DIHYDRO-1H-PHENALEN-2-YL)-N'-BUTYLUREA

EXAMPLE 30
N-(4-METHOXY-2,3-DIHYDRO-1H-PHENALEN-2-YL)-N'-HEXYLUREA

EXAMPLE 31
N-(4-METHOXY-2,3-DIHYDRO-1H-PHENALEN-2-YL)-N'-CYCLOPROPYLUREA

EXAMPLE 32
N-(4-METHOXY-2,3-DIHYDRO-1H-PHENALEN-2-YL)-N'-CYCLOBUTYLUREA

EXAMPLE 33
N-(4-METHOXY-2,3-DIHYDRO-1H-PHENALEN-2-YL)-N'-CYCLOHEXYLUREA

EXAMPLE 34
N-(4-METHOXY-2,3-DIHYDRO-1H-PHENALEN-2-YL)-N'-METHYLTHIOUREA

EXAMPLE 35
N-(4-METHOXY-2,3-DIHYDRO-1H-PHENALEN-2-YL)-N'-PROPYLTHIOUREA

EXAMPLE 36
N-(4-METHOXY-2,3-DIHYDRO-1H-PHENALEN-2-YL)-N'-CYCLOPROPYLTHIOUREA

EXAMPLE 37

N-(2,3-DIHYDRO-1H-PHENALEN-2-YL) PROPIONAMIDE (2nd process)

Working as in Example 3, but starting with Preparation 2, the title compound is obtained.

EXAMPLES 38 TO 46

Working as in Example 3, but starting with Preparations 36 to 38 and using the appropriate acylchlorides, the following compounds are obtained:

EXAMPLE 38

N-ETHYL-N-(4-METHYL-2,3-DIHYDRO-1H-PHENALEN-2-YL)ACETAMIDE

EXAMPLE 39

N-ETHYL-N-(4-METHYL-2,3-DIHYDRO-1H-PHENALEN-2-YL)PROPIONAMIDE

EXAMPLE 40

N-ETHYL-N-(4-METHYL-2,3-DIHYDRO-1H-PHENALEN-2-YL) CYCLOPROPYLCARBOXAMIDE

EXAMPLE 41

N-METHYL-N-(2,3-DIHYDRO-1H-PHENALEN-2-YL)ACETAMIDE

EXAMPLE 42

N-METHYL-N-(2,3-DIHYDRO-1H-PHENALEN-2-YL)PROPIONAMIDE

EXAMPLE 43

N-METHYL-N-(2,3-DIHYDRO-1H-PHENALEN-2-YL)CYCLOPROPYLCARBOXAMIDE

EXAMPLE 44

N-(5-METHOXY-2,3-DIHYDRO-1H-PHENALEN-2-YL)ACETAMIDE

EXAMPLE 45

N-(5-METHOXY-2,3-DIHYDRO-1H-PHENALEN-2-YL)PROPIONAMIDE

EXAMPLE 46

N-(5-METHOXY-2,3-DIHYDRO-1H-PHENALEN-2-YL)CYCLOPROPYLCARBOXAMIDE

EXAMPLE 47

N-(4,9-DIMETHOXY-2,3-DIHYDRO-1H-PHENALEN-2-YL)ACETAMIDE

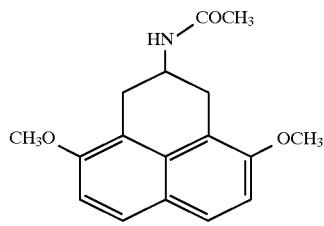

Stage A: N-(1-oxo-4,9-dimethoxy-2,3-dihydro-1H-phenalen-2-yl)acetamide

The compound obtained in Preparation 33 (5 mmol; 1.65 g) is dissolved in 10 cm³ of acetic anhydride and the reaction medium is maintained at the reflux temperature of the solvent for 40 min. The excess anhydride is evaporated to dryness with a trolley pump in order to isolate the 2-methyl-4-[(2,7-dimethoxynaphth-1-yl)methyl]oxazolin-5-one, which is used without further purification. 30 cm³ of anhydrous $CH_2Cl_2$ and aluminum chloride (18 mmol; 2.37 g) are introduced into a three-necked flask placed under an inert atmosphere, followed by dropwise addition of 2-methyl-4-[(2,7-dimethoxynaphth-1-yl)methyl]oxazolin-5-one (6 mmol; 1.78 g) dissolved in 40 cm³ of the same solvent. The reaction medium is maintained at 60° C. for 2 h and, after cooling, is then poured onto an ice/concentrated HCl mixture and stirred for 1 h. The organic phase is recovered and the aqueous phase is extracted several times with $CH_2Cl_2$. The combined organic phases are dried over $MgSO_4$ and then evaporated. The residue is purified by chromatography on a column of silica gel (particle size 60–200 µm); eluent: $CH_2Cl_2$ then $CH_2Cl_2$:MeOH 99:1 v/v. N-(1-oxo-4,9-dimethoxy-2,3-dihydro-1H-phenalen-2-yl)acetamide (α) and N-(1-oxo-9-hydroxy-4-methoxy-2,3-dihydro-1H-phenalen-2-yl)acetamide (β) are obtained.

α:

Yield: 10% m.p.>260° C.

$^1$H NMR (CDCl$_3$) δ(ppm): 2.11 (s, 3H, COCH$_3$); 2.59–2.74 (m, 1H, AB of a CHCH$_2$ ABX system); 3.94 (s, 3H, OCH$_3$); 4.04 (s, 3H, OCH$_3$); 4.19–4.30 (dd, 1H, $J_{BX}$=7 Hz, $J_{AB}$=16 Hz, AB of a CHCH$_2$ ABX system); 4.88 (m, 1H, CH); 6.97 (bs, 1H, NH); 7.12–7.18 (2d, 2H, J=9 Hz, H$_{ar}$); 7.71 (d 1H, J=9 Hz, H$_{ar}$); 7.96 (d, 1H, J=9 Hz, H$_{ar}$).

β:

Yield: 12% m.p.>260° C.

$^1$H NMR (CDCl$_3$) δ(ppm): 2.15 (s, 3H, COCH$_3$); 2.67–2.74 (dd, 1H, AB of a CHCH$_2$ ABX system); 3.94 (s, 3H, OCH$_3$); 4.17–4.22 (dd, 1H, $J_{BX}$=8 Hz, $J_{AB}$=16 Hz, AB of a CHCH$_2$ ABX system); 4.94–4.97 (m, 1H, CH); 6.52 (bs, 1H, NH); 6.97 (d, 1H, J=9 Hz, H$_8$); 7.12 (d 1H, J=9 Hz, H$_5$); 7.67 (d, 1H, J=9 Hz, H$_7$); 7.90 (d, 1H, J=9 Hz, H$_6$); 12.35 (s, 1H, OH).

Stage B: N-(4,9-dimethoxy-2,3-dihydro-1H-phenalen-2-yl)acetamide

Procedure:

The N-(1-oxo-4,9-dimethoxy-2,3-dihydro-1H-phenalen-2-yl)acetamide obtained in the above stage (0.6 mmol; 0.17 g) is dissolved in 25 cm³ of acetic acid and, after flushing several times with argon, 10% Pd/C (85 mg) is added and the reaction medium is placed under an H$_2$ atmosphere. Stirring is maintained for 28 h at room temperature and the palladium is filtered off on Celite. The acetic acid is evaporated to dryness and the residue is purified by chromatography on a column of silica gel (particle size 60–200 µm); eluent $CH_2Cl_2$:MeOH 99:1 v/v, to give the expected product.

Yield: 43% TLC (silica): Rf=0.35 ($CH_2Cl_2$:MeOH 95:5) m.p.=254° C.

$^1$H NMR (DMSO-d$_6$) δ(ppm): 1.83 (s, 3H, COCH$_3$); 2.53–2.60 (dd, 2H, $J_{AX}$=10 Hz, $J_{AB}$=16 Hz, AB of a CHCH$_2$ ABX system); 3.23–3.28 (dd, 2H, $J_{BX}$=4 Hz, $J_{AB}$=16 Hz, AB of a CHCH$_2$ ABX system); 3.86 (s, 6H, 2xOCH$_3$); 3.89–3.95 (m, 1H, CH); 7.22 (d, 1H, J=9 Hz, H$_5$ and H$_8$); 7.71 (d, 2H, J=9 Hz, H$_6$ and H$_7$); 7.99 (d, 1H, NH).

$^{13}$C NMR (DMSO-d$_6$) δ(ppm): 22.77 (COCH$_3$); 29.02 (2 CH$_2$); 43.64 (CHNH); 55.58 (2 OCH$_3$); 111.12 (C$_{ar}$); 116.74 (C$_{ar}$); 123.7 (C$_{ar}$); 127.05 (C$_{ar}$); 130.7 (C$_{ar}$); 153.07 (C$_{ar}$); 168.83 (COCH$_3$).

| Elemental analysis: Formula: $C_{17}H_{19}NO_3$ M = 255.3 | | | |
|---|---|---|---|
| | C % | H % | N % |
| Calculated | 71.55 | 6.71 | 4.91 |
| Found | 70.59 | 6.79 | 4.80 |

EXAMPLES 48 AND 49

Working as in Example 47, but using suitable acylation reagents, the compounds of the following examples are obtained:

EXAMPLE 48

N-(4,9-DIMETHOXY-2,3-DIHYDRO-1H-PHENALEN-2-YL)PROPIONAMIDE

EXAMPLE 49

N-(4,9-DIMETHOXY-2,3-DIHYDRO-1H-PHENALEN-2-YL) CYCLOPROPYLCARBOXAMIDE

EXAMPLES 50 TO 61

Working as in Example 1, but starting with Preparations 21 to 32, the compounds of the following examples are obtained;

EXAMPLE 50

N-(1,3,4,5-TETRAHYDROBENZO[cd]INDOL-4-YL)ACETAMIDE

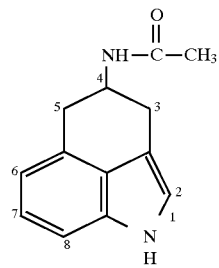

Example 50

EXAMPLE 51

N-(1,3,4,5-TETRAHYDRO-6-METHOXYBENZO[cd]INDOL-4-YL)ACETAMIDE

EXAMPLE 52

N-(1,3,4,5-TETRAHYDRO-6-BROMOBENZO[cd]INDOL-4-YL)ACETAMIDE

EXAMPLE 53

N-(1,3,4,5-TETRAHYDRO-6-ETHYLBENZO[cd]INDOL-4-YL)ACETAMIDE

EXAMPLE 54

N-(3,4,5-TRIHYDROBENZO[cd]BENZOFURAN-4-YL)ACETAMIDE

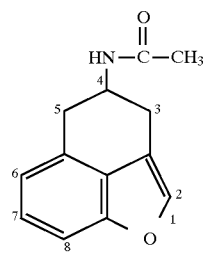

Example 54

EXAMPLE 55

N-(3,4,5-TRIHYDRO-6-METHOXYBENZO[cd]BENZOFURAN-4-YL)ACETAMIDE

EXAMPLE 56

N-(3,4,5-TRIHYDRO-6-BROMOBENZO[cd]BENZOFURAN-4-YL)ACETAMIDE

EXAMPLE 57

N-(3,4,5-TRIHYDRO-6-ETHYLBENZO[cd]BENZOFURAN-4-YL)ACETAMIDE

EXAMPLE 58

N-(3,4,5-TRIHYDROBENZO[cd]BENZOTHIOPHEN-4-YL)ACETAMIDE

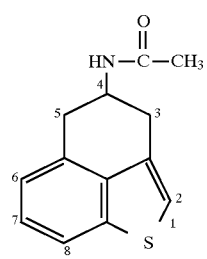

Example 58

EXAMPLE 59

N-(3,4,5-TRIHYDRO-6-METHOXYBENZO[cd]BENZOTHIOPHEN-4-YL)ACETAMIDE

EXAMPLE 60

N-(3,4,5-TRIHYDRO-6-BROMOBENZO[cd]BENZOTHIOPHEN-4-YL)ACETAMIDE

EXAMPLE 61

N-(3,4,5-TRIHYDRO-6-ETHYLBENZO[cd]BENZOTHIOPHEN-4-YL)ACETAMIDE

EXAMPLE 62

N-(4-METHOXY-9-HYDROXY-2,3-DIHYDRO-1H-PHENALEN-2-YL)ACETAMIDE

Procedure:

Starting with 0.7 mmol (200 mg) of N-(1-oxo-9-hydroxy-4-methoxy-2,3-dihydro-1H-phenalen-2-yl)acetamide obtained in Stage A of Example 47 and 100 mg of 10% Pd/C in 12 cm$^3$ of acetic acid, and under the same conditions as in Stage B of Example 47, the title compound is obtained, which is purified by simple crystallization from dichloromethane.

Yield: 37% TLC (silica): Rf=0.18 (CH$_2$Cl$_2$:MeOH 95:5) m.p.>254° C.

$^1$H NMR (CD$_3$COCD$_3$) δ(ppm): 1.86 (s, 3H, COCH$_3$); 2.67–2.79 (dd, 2H, AB of a CHCH$_2$ ABX system); 2.99 (bs, 1H, OH); 3.33–3.41 (dd, 2H, AB of a CHCH$_2$ ABX system); 3.89 (s, 3H, OCH$_3$); 4.18–4.32 (m, 1H, CH); 7.01 (d, 1H, J=9 Hz, H$_8$); 7.12 (d, 1H, J=9 Hz, H$_5$); 7.25 (bs, 1H, NH); 7.50 (d, 1H, J=9 Hz, H$_7$); 7.62 (d, 1H, J=9 Hz, H$_6$).

$^{13}$C NMR (DMSO-d$_6$) δ(ppm): 22.79 (COCH$_3$); 29.16 (2 CH$_2$); 43.67 (CHNH); 55.90 (OCH$_3$); 109.94 (C$_{ar}$); 111.12 (C$_{ar}$); 113.78 (C$_{ar}$); 116.55 (C$_{ar}$); 123.0 (C$_{ar}$); 126.47 (C$_{ar}$); 126.58 (C$_{ar}$); 130.1 (C$_{ar}$); 131.07 (C$_{ar}$); 151.29 (C$_{ar}$); 152.96 (C$_{ar}$); 168.74 (COCH$_3$).

EXAMPLE 63

10-METHOXY-2-ACETAMIDO-1,2,3,4-TETRAHYDROPHENANTHRENE

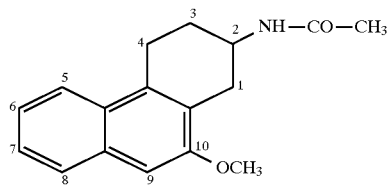

The compound obtained in Preparation 39 (0.11 g; 0.5 mmol) is dissolved in dichloromethane in the presence of triethylamine (1.2 eq.). Acetyl chloride is added, at 0° C., and the reaction medium is stirred for 1 h at room temperature. The expected compound is purified by chromatography on a column of silica (eluent: 5% methanol:CH$_2$Cl$_2$).

Yield: 56%

$^1$H NMR (200 MHz, CDCl$_3$): δ7.81 (d, 1H), 7.64 (d, 1H), 7.38–7.26 (m, 2H), 6.9 (s, 1H), 5.34 (d, 1H), 4.33–4.2 (m, 1H), 3.83 (s, 3H), 3.1–3.04 (m, 2H), 2.67–2.44 (m, 2H), 2.11–2.01 (m, 1H), 1.99–1.7 (m, 1H), 1.90 (s, 3H), 1.83–1.69 (m, 1H)

EXAMPLES 64 TO 67

Working as in Example 63, but using suitable acylation reagents, the compounds of the following examples are obtained:

EXAMPLE 64

10-METHOXY-2-PROPIONAMIDO-1,2,3,4-TETRAHYDROPHENANTHRENE

EXAMPLE 65

10-METHOXY-2-TRIFLUOROACETAMIDO-1,2,3,4-TETRAHYDROPHENANTHRENE

EXAMPLE 66

10-METHOXY-2-CYCLOPROPYLCARBOXAMIDO-1,2,3,4-TETRAHYDROPHENANTHRENE

EXAMPLE 67

10-METHOXY-2-CYCLOBUTYLCARBOXAMIDO-1,2,3,4-TETRAHYDROPHENANTHRENE

EXAMPLE 68

10-METHOXY-3-ACETAMIDO-1,2,3,4-TETRAHYDROPHENANTHRENE

Working as in Example 63, but starting with Preparation 40, the title compound is obtained.

EXAMPLE 69

9-METHOXY-2-ACETAMIDO-1,2,3,4-TETRAHYDROANTHR-ACENE

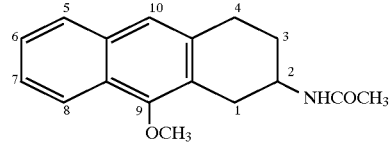

Working as in Example 63, but starting with Preparation 41, the title compound is obtained.

EXAMPLES 70 TO 73

Working as in Example 69, but using suitable acylation reagents, the compounds of the following examples are obtained.

EXAMPLE 70

9-METHOXY-2-PROPIONAMIDO-1,2,3,4-TETRAHYDROANTHRACENE

EXAMPLE 71

9-METHOXY-2-TRIFLUOROACETAMIDO-1,2,3,4-TETRAHYDROANTHRACENE

EXAMPLE 72

9-METHOXY-2-CYCLOPROPYLCARBOXAMIDO-1,2,3,4-TETRAHYDROANTHRACENE

EXAMPLE 73

9-METHOXY-2-CYCLOBUTYLCARBOXAMIDO-1,2,3,4-TETRAHYDROANTHRACENE

EXAMPLE 74

N-(1-METHOXY-2,3-DIHYDRO-1H-PHENALEN-2-YL-)ACETAMIDE

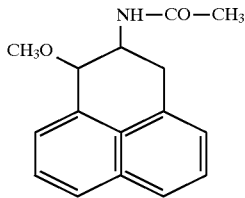

The N-(1-hydroxy-2,3-dihydro-1H-phenalen-2-yl) acetamide obtained is stage C of Example 1 (1 mmol, 290 mg) is dissolved in 10 cm³ of anhydrous DMF. Under an inert atmosphere, NaH (1 mmol, 0.05 g of 60% in oil suspension) and then methyl iodide (0.09 cm³, 1.2 eq) are added in the reaction mixture. Stirring is maintained at ambiant temperature for 4 h30 and the solvent is evaporated. The residue is taken up in $CH_2Cl_2$ and the solution is filtrated. The filtrate is evaporated and purified by chromatography on silica gel (particle size 60–200 μm); eluent: $CH_2Cl_2$:MeOH 99:1 v/v. The title product is isolated. This is and amorphous product, which is a diastereoisomer mixture. TLC (silica): Rf: 0.64 (MeOH:$CH_2Cl_2$ 5: 95).

$^1$H NMR (CDCl$_3$) δ(ppm): 1.78 (s, 3H, COCH$_3$) 2.93–3.03 (m, 1H, AB of a CHCH$_2$ ABX system); 3.42 (s, 3H, OCH$_3$); 3.66–3.77 (m, 1H, AB of a CH CH$_2$ ABX system) 4.48 (d, 1H, CHOMe); 4.78–4.90 (m, 1H, CH); 5.18 (s, 1H, NH); 7.32–7.55 (m, 4H, H$_{ar}$) 7.79 (d, 1H, H$_{ar}$); 7.88 (d, 1H, H$_{ar}$).

PHARMACOLOGICAL STUDY

EXAMPLE A: STUDY OF THE ACUTE TOXICITY

The acute toxicity was assessed after oral administration to groups of 8 mice (26±2 grams). The animals were observed at regular intervals throughout the first day and daily for the two weeks following the treatment. The LD$_{50}$, leading to the death of 50% of the animals, was evaluated.

The LD$_{50}$ of the test products is greater than 1000 mg kg$^{-1}$ for most of the compounds studied, thereby indicating the low toxicity of the compounds of the invention.

EXAMPLE B: STUDY OF BINDING TO THE MELATONIN RECEPTORS

B1) Study on sheep pars tuberalis cells

The studies of the binding of the compounds of the invention to the melatonin receptors were performed according to the standard techniques, on sheep pars tuberalis cells. The pars tuberalis of the adenohypophysis is indeed characterized, in mammals, by a high density of melatonin receptors (Journal of Neuroendocrinology 1989, Vol. (1), pp 1–4).

PROCEDURE

1) Sheep pars tuberalis membranes are prepared and used as target tissue in saturation experiments in order to determine the binding capacities and affinities for 2-[$^{125}$I]-iodomelatonin.

2) The sheep pars tuberalis membranes are used as target tissue, with various test compounds, in competitive binding experiments relative to 2-[$^{125}$I]-iodomelatonin.

Each experiment is performed in triplicate and a range of different concentrations is tested for each compound.

The results make it possible to determine, after statistical treatment, the binding affinities of the test compound.

RESULTS

It is seen that the compounds of the invention possess a powerful affinity for the melatonin receptors, this affinity being stronger than that for melatonin itself.

B2) Study on chick (Gallus domesticus) brain cell membranes

The animals used are 12-day old chicks (Gallus domesticus) They are sacrificed between 13.00 h and 17.00 h on the day of their arrival. The brains are rapidly removed and frozen at −200° C. and then stored at −80° C. The membranes are prepared according to the method described by Yuan and Pang (Journal of Endocrinology 1991, 128, pp 475–482). 2-[$^{125}$I]-iodo melatonin is incubated in the presence of the membranes in a solution buffered to pH 7.4 for 60 min at 25° C. After this period, the membrane suspension is filtered (Whatman GF/C). The radioactivity retained on the filter is determined using a Beckman® LS 6000 liquid scintillation counter.

The products used are:

2-[$^{125}$I]-iodomelatonin melatonin common products test compounds

In primary screening, the molecules are tested at 2 concentrations (10$^{-7}$ and 10$^{-5}$M). Each result is the average of n=3 independent measurements. The test compounds are subjected to a quantitative determination of their efficacy (IC$_{50}$). They are used at 10 different concentrations.

Thus, the IC$_{50}$ values found for the preferred compounds of the invention, which correspond to the values of the affinity, show that the binding of the test compounds is very powerful.

It also turns out that the compounds of the invention have an original activity profile, since they appear to be antagonists on the sheep pars tuberalis model (Example B-1) and agonists on the melanophore aggregation model (Example B-2).

EXAMPLE B-1

EXPERIMENTAL PROCEDURE

This study is performed on a culture of sheep pars tuberalis cells and makes it possible to characterize the activity of the test compounds on the production of cAMP induced by forskolin. (Morgan et al. J. Molecular Endocrinol. 1989, 3, pp. R5–R8).

The compounds ($1.10^{-5}M$) are tested alone and are compared with melatonin ($1.10^{-9}M$) in order to detect their capacity to inhibit the production of cAMP stimulated by forskolin ($1.10^{-6}M$) or, in combination with melatonin, in order to detect an antagonist activity. These experiments are performed in triplicate. Two cAMP indices are thus determined, one for the test compound alone (cAMP [D]) and the other for the test compound in combination with melatonin (cAMP [D/M]). They are calculated as follows:

cAMP [D]=([F]–[F/D])/([F]–[F/M])
cAMP [D/M]=([F]–[F/D/M])/([F]–[F/M])
where
- [F]: cellular cAMP level after stimulation with 1 μM of forskolin
- [F/D]: cellular cAMP level after stimulation with 1 μM of forskolin in the presence of the test compound (1 or 10 nM).
- [F/M]: cellular cAMP level after stimulation with 1 μM of forskolin in the presence of melatonin (1 or 10 μM).
- [F/D/M]: cellular cAMP level after stimulation with 1 μM of forskolin in the presence of melatonin (1 or 10 nM) and of the test compound (1 or 10 μM).

A compound which is a pure agonist has a cAMP [D] and a cAMP [D/M] equal to 1.

EXAMPLE B-2
EXPERIMENTAL PROCEDURE

The neural crests of 20 *Xenopus laevis* embryos are disected and dispersed as small aggregates in Petri dishes containing culture medium (L-15 diluted with 10% fetal calf serum). After 7 days, a certain number (20–200) of melanophores may be seen in the Petri dish among many other cells (nerve cells and muscle cells for example) which are distinct therefrom.

At rest, the melanophores are uniformly filled with granules of pigment when melatonin is added to the medium, the pigment granules condensing around the nucleus. The modification of the cell surface occupied by the pigments is quantified by imagery as a function of the concentration of melatonin added. The melatonin has an $EC_{50}$ (50% effective concentration) of about 10 pM. The compounds are tested for their capacity to mimic or to abolish this pigmentary condensation induced by melatonin (10 nM).

EXAMPLE C: FOUR-PLATE TEST

The products of the invention are administered esophagially to groups of ten mice. One batch receives gum syrup. 30 min after administration of the products to be studied, the animals are placed in chambers the floor of which comprises four metal plates. Each time the animal passes from one plate to another, it receives a mild electric discharge (0.35 mA). The number of passages is recorded for one minute. After administration, the compounds of the invention significantly increase the number of passages, which shows the anxiolytic activity of the derivatives of the invention.

EXAMPLE D: COMPOUNDS OF THE INVENTION ON THE CIRCADIAN RHYTHMS OF RAT LOCOMOTOR ACTIVITY

The involvement of melatonin in driving, via the alternating day/night cycle, most of the physiological, biochemical and behavioral circadium rhythms has made it possible to establish a pharmacological model for the search for melatoninergic ligands.

The effects of the molecules are tested on a number of parameters and in particular on the circadian rhythms of locomotor activity, which represent a reliable marker of the activity of the endogenous circadian clock.

In this study, the effects of such molecules on a particular experimental model, namely a rat placed in temporal isolation (permanent darkness), are evaluated

EXPERIMENTAL PROCEDURE

On their arrival at the laboratory, one-month-old male Long Evans rats are subjected to a lighting cycle of 12 h of light per 24 h (12:12 LD)).

After 2 to 3 weeks of adaptation, they are placed in cages equipped with a wheel connected to a recording system so as to detect the phases of locomotor activity and thus to monitor the nyctohemeral (LD) or circadian (DD) rhythms.

As soon as the rhythms recorded show evidence of being stably driven by the 12:12 LD lighting cycle, the rats are placed in permanent darkness (DD).

Two to three weeks later, when the free, non-driven pattern (rhythm reflecting that of the endogenous clock) is clearly established, the rats receive a daily administration of the test molecule.

The observations are made by virtue of visualization of the rhythms of activity:
- rhythms of activity driven by the lighting rhythm,
- disappearance of the driving pattern for the rhythms in permanent darkness,
- rhythms driven by the daily administration of the molecule; transient or long-lasting effect.

A software program makes it possible:
- to measure the duration and intensity of the activity, the period of the rhythm in the animals under free, non-driven conditions and during the experiment,
- possibly to demonstrate, by spectral analysis, the existence of circadian and non-circadian components.

RESULTS:

It is clearly seen that the compounds of the invention make it possible to have a powerful effect on the circadian rhythm via the melatoninergic system.

EXAMPLE E: ACTIVITY OF THE PRODUCTS OF THE INVENTION ON ISCHEMIC MICROCIRCULATION

The experimental study was performed on the cremaster muscles of male rats (Sprague-Dawley) after ligature of the common iliac artery.

The muscles were placed in a transparent chamber, infused with a solution of bicarbonate buffer equilibrated with a 5/95% $CO_2/N_2$ gas mixture. The speed of the red blood cells and the diameter of the arterioles of the first or second order irrigating the cremaster were measured, and the arteriolar blood flow was calculated. Identical information was obtained for four types of venule.

The same type of measurement was carried out simultaneously:
- on the cremaster infused normally,
- on the cremaster under ligature, that is to say the cremaster under ischemia 2, 7, 14 and 21 days after ligature.

Two groups of animals were studied:
- a control group without treatment,
- a group treated orally with a product of the invention, at an amount of 0.1 mg $kg^{-1}$ per day.

No difference was observed in the speed of the blood cells or in the diameter of the vessels in the cremaster muscles irrigated normally in the animals treated, when compared with the controls.

On the other hand, in the cremaster muscle under ischemia, the average diameter of the arterioles was improved in the treated animals compared with the controls. The speed of the red blood cells was standardized by a 21-day treatment.

In point of fact, in the treated animals, the speed of the red blood cells and the blood flow measured 7 days after the ligature showed no significant difference with the values obtained in the non-ischemic cremaster. These results are obtained without modification of the arterial pressure.

These results indicate that chronic treatment with a compound of the invention improves the microcirculation and the blood irrigation of regions under ischemia.

EXAMPLE F: STIMULATION OF THE IMMUNE RESPONSES

Sheep red blood cells were administered to groups of six mice. These groups of mice were then treated subcutaneously with the compounds of the invention for six days and a control group was treated with a placebo. The mice were subsequently left alone for four weeks and were then given a repeat injection of sheep red blood cells without receiving further administrations of product of the invention. The immune response was evaluated 3 days after the repeat injection. It is statistically higher in the group treated with the compounds of the invention.

EXAMPLE G: INHIBITION OF OVULATION

Adult female rats with regular four-day cycles are used.

Daily vaginal scrapes were performed and rats were selected after they displayed at least two consecutive four-day cycles.

Each cycle consisted of two days of diestrus, one day of proestrus and one day of estrus.

On the afternoon of the day of proestrus, luteinizing hormone is released into the blood from the hypophysis. This hormone induces ovulation, reflected in the presence of eggs in the oviduct on the day of estrus. The compounds of the invention are administered orally at midday on the day of estrus. The treated and control rats are sacrificed on the day of estrus. The oviducts are examined. A significant percentage decrease in the number of eggs in the oviducts of the treated rats is observed.

EXAMPLE H: ANTIARRYTHMIC ACTIVITY

PROCEDURE (ref: Lawson J. N. et al. J. Pharmacol. Exper. Therap. 1968, 160, pp 22–31)

The test substance is administered intraperitoneally to a group of 3 mice 30 min before exposure to anesthesia by chloroform. The animals are then observed for 15 min. The absence of recording of arrythmia and of cardiac rates above 200 beats/min (control: 400–480 beats/min) in the animals indicates at least significant protection.

EXAMPLE I: PHARMACEUTICAL COMPOSITION: COMPOUNDS

| 1000 tablets containing a 5 mg dose of N-(2,3-dihydro-1H-phenalen-2-yl)acetamide | |
|---|---|
| N-(2,3-Dihydro-1H-phenalen-2-yl)acetamide | 5 g |
| Wheat starch | 20 g |
| Corn starch | 20 g |
| Lactose | 30 g |
| Magnesium stearate | 2 g |
| Silica | 1 g |
| Hydroxypropylcellulose | 2 g |

We claim:
1. A compound selected from those of formula (I):

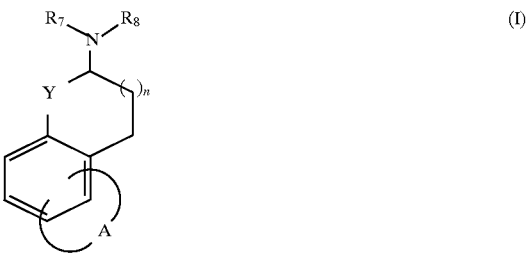

in which A forms, with the group to which it is attached, a tricyclic compound ($A_1$)

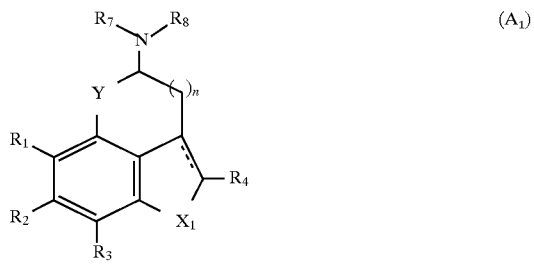

in which:

$R^1$, $R_2$, $R_3$ and $R_4$ represent, independently of each other, hydrogen or a radical chosen from halogen, hydroxyl, Ra and —O—Ra; with Ra representing a radical chosen from alkyl, alkyl substituted with one or more halogens, alkenyl, alkynyl, cycloalkyl, cycloalkylalkyl, aryl, substituted aryl, arylalkyl, and substituted arylalkyl;

$X_1$ represents a group chosen from sulfur, oxygen, and —N($R_{14}$)— where $R_{14}$ represents hydrogen or a radical chosen from alkyl, aryl, arylalkyl, substituted aryl, and substituted arylalkyl, the bond - - - - means that this bond is a double bond, Y represents a group —C($R_9$)($R_{10}$)— in which $R_9$ and $R_{10}$ represent, independently of each other, hydrogen, alkyl or alkoxy, n represents 1 to 3, inclusive, $R_7$ represents hydrogen or a radical $R_7$' chosen from alkyl, aryl, arylalkyl, substituted aryl, and substituted arylalkyl and $R_8$ represents:

a group of formula —CO—$R_{11}$ in which $R_{11}$ represents a radical $R_{12}$ with $R_{12}$ representing hydrogen or a radical chosen from alkyl, alkyl substituted with one or more halogens, alkenyl, alkynyl, cycloalkyl, cycloalkylalkyl, aryl, substituted aryl, arylalkyl and substituted arylalkyl, or $R_{11}$ represents a radical —NH—$R_{13}$, with $R_{13}$ representing hydrogen or a radical chosen from alkyl, alkyl substituted with one or more halogens, alkenyl, alkynyl, cycloalkyl, cycloalkylalkyl, aryl, substituted aryl, arylalkyl, and substituted arylalkyl;

or $R_8$ represents a group of formula —CS—$R_{11}$ in which $R_{11}$ is as defined above with the proviso
that, if $X_1$ represents —NH— or —N(CH$_3$)—, then $R_1$ cannot be hydrogen or halogen, its enantiomers and diastereoisomers and its addition salts thereof with a pharmaceutically-acceptable base, it being understood that:

the terms "alkyl" and "alkoxy" denote linear or branched radicals of 1 to 6 carbon atoms, inclusive, the terms "alkenyl" and "alkynyl" represent unsaturated linear or branched radicals of 2 to 6 carbon atoms, inclusive, the term "cycloalkyl" denotes a cyclic group of 3 to 8 carbon atoms, inclusive, the term "aryl" denotes naphthyl, phenyl, or pyridyl, the expression "substituted" associated with the terms "aryl" and "arylalkyl" means that these groups are substituted with one or more radicals chosen from halogen, alkyl, alkyl substituted with one or more halogens, alkoxy, and hydroxyl.

2. A compound of claim 1 wherein $X_1$ is sulfur.

3. A compound of claim 1 wherein $X_1$ is oxygen.

4. A compound of claim 1 wherein $X_1$ is —N(R$_{14}$)—.

5. A compound of claim 1 which is N-(1,3,4,5-tetrahydro-6-methoxybenzo[cd]indol-4-yl)acetamide.

6. A compound of claim 1 which is N-(1,3,4,5-tetrahydro-6-ethylbenzo[cd]indol-4-yl)acetamide.

7. A compound of claim 1 which is N-(3,4,5-trihydrobenzo[cd]-benzofuran-4-yl)acetamide.

8. A compound of claim 1 which is N-(3,4,5-trihydro-6-methoxybenzo[cd]benzofuran-4-yl)acetamide.

9. A compound of claim 1 which is N-(3,4,5-trihydro-6-bromobenzo[cd]benzofuran-4-yl)acetamide.

10. A compound of claim 1 which is N-(3,4,5-trihydro-6-ethylbenzo[cd]benzofuran-4-yl)acetamide.

11. A compound of claim 1 which is N-(3,4,5-trihydrobenzo[cd]-benzothiophen-4-yl)acetamide.

12. A compound of claim 1 which is N-(3,4,5-trihydro-6-methoxybenzo[cd]benzothiophen-4-yl)acetamide.

13. A compound of claim 1 which is N-(3,4,5-trihydro-6-bromobenzo[cd]benzothiophen-4-yl)acetamide.

14. A compound of claim 1 which is N-(3,4,5-trihydro-6-ethylbenzo[cd]benzothiophen-4-yl)acetamide.

15. A pharmaceutical composition containing a compound of claim 1 in combination with one or more pharmaceutically-acceptable excipients.

16. A method of treating a mammal afflicted with a disorder of the melatoninergic system comprising the step of administering to said mammal an effective amount of a compound as claimed in claim 1 in order to alleviate the said disorder.

17. A method of treating a mammal afflicted with a sleep disorder comprising the step of administering to said mammal an effective amount of a compound as claimed in claim 1 in order to alleviate the said disorder.

* * * * *

UNITED STATES PATENT AND TRADEMARK OFFICE
CERTIFICATE OF CORRECTION

PATENT NO. : 5,849,781
DATED : Dec. 15, 1998
INVENTOR(S) : M. Langlois, M. Mathe-Allainmat, P. Delagrange, P. Renard, B. Guardiola It is certified that error appears in the above-indentified patent and that said Letters Patent is hereby corrected as shown below:

Title Page, OTHER PUBLICATIONS, #1, line 4: "tuuberalis" should read -- tuberalis --. Form PTO 1449, <u>Other Prior Art</u>.

Title Page, OTHER PUBLICATIONS, line 18: "1562272h" should read -- 156272h --. Form PTO 1449, <u>Other Prior Art</u>.

Column 3, line 27: "X," should read -- $X_1$ --.
    Page 4, line 3

Column 9, line 45: "HN" in the formula should read

Column 46, line 17: The "(a)" at the end of the line, should read -- (α) --. Page 59, line 3

Column 57, line 5: Delete the word "thereof" at the

Signed and Sealed this

Eighteenth Day of May, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,849,781
DATED : December 15, 1998
INVENTOR(S) : M. Langlois, M. Mathe-Allainmat, P. Delagrange, P. Renard, B. Guardiola It is certified that error appears in the above-identified patent and that said Letters Patent is hereby corrected as shown below:

Title page, OTHER PUBLICATIONS,
1, Line 4, "tuuberalis" should read -- tuberalis --.
Line 18, "1562272h" should read -- 156272h --.

Column 3,
Line 27, "X," should read -- $X_1$ --.

Column 9,
Line 45, "HN" in the formula should read -- N --.

Column 46,.
Line 17, The "(a)" at the end of the line, should read -- ($\alpha$) --.

Column 57,
Line 5, delete the word "thereof" at the beginning of the line.

This ceritificate supercedes certificate of correction issued May 18, 1999.

Signed and Sealed this

Thirtieth Day of October, 2001

Attest:

*Nicholas P. Godici*

NICHOLAS P. GODICI
*Attesting Officer*     *Acting Director of the United States Patent and Trademark Office*